US012558094B2

(12) United States Patent
Shelton, IV et al.

(10) Patent No.: US 12,558,094 B2
(45) Date of Patent: Feb. 24, 2026

(54) SLED RETENTION AND ALIGNMENT FEATURES FOR SURGICAL STAPLER

(71) Applicant: Cilag GmbH International, Zug (CH)

(72) Inventors: Frederick E. Shelton, IV, New Vienna, OH (US); Nicholas Fanelli, Morrow, OH (US); Kevin M. Fiebig, Cincinnati, OH (US); John P. May, Mason, OH (US); Nicholas A. Wilson, Montgomery, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/758,887

(22) Filed: Jun. 28, 2024

(65) Prior Publication Data

US 2026/0000400 A1 Jan. 1, 2026

(51) Int. Cl.
*A61B 17/072* (2006.01)
*A61B 17/068* (2006.01)

(52) U.S. Cl.
CPC ................... *A61B 17/07207* (2013.01); *A61B 2017/07271* (2013.01); *A61B 2017/07278* (2013.01)

(58) Field of Classification Search
CPC ................ A61B 17/072; A61B 17/068; A61B 17/07207
USPC ....................................... 227/175.1
See application file for complete search history.

(56) References Cited

U.S. PATENT DOCUMENTS

| | | | |
|---|---|---|---|
| 8,453,914 B2 | 6/2013 | Laurent et al. | |
| 9,186,142 B2 | 11/2015 | Fanelli et al. | |
| 9,717,497 B2 | 8/2017 | Zerkle et al. | |
| 9,808,248 B2 | 11/2017 | Hoffman | |
| 9,839,421 B2 | 12/2017 | Zerkle et al. | |
| 9,867,615 B2 * | 1/2018 | Fanelli | A61B 17/07207 |
| 10,092,292 B2 | 10/2018 | Boudreaux et al. | |
| 10,130,359 B2 | 11/2018 | Hess et al. | |
| 10,702,271 B2 * | 7/2020 | Aranyi | A61B 17/07207 |
| 11,116,505 B2 * | 9/2021 | Vendely | A61B 17/07292 |
| 11,229,433 B2 | 1/2022 | Schings et al. | |
| 11,272,935 B2 * | 3/2022 | Bakos | A61B 17/07207 |
| 11,540,826 B2 | 1/2023 | Nalagatla et al. | |
| 11,678,882 B2 | 6/2023 | Shelton, IV et al. | |
| 2018/0168605 A1 * | 6/2018 | Baber | A61B 17/07207 |

OTHER PUBLICATIONS

U.S. Appl. No. 18/588,094.
U.S. Appl. No. 18/588,147.

(Continued)

*Primary Examiner* — Praachi M Pathak
(74) *Attorney, Agent, or Firm* — FBT Gibbons LLP

(57) ABSTRACT

A sled (182) for a surgical stapler, the sled including: a base, a plurality of rails, a first detent, and a second detent. The base being configured to translate distally relative to a jaw of the surgical stapler through a firing stroke to eject a plurality of staples into tissue. The plurality of rails (184, 185) extending upwardly from the base and configured to guide distal translation of the sled within the jaw through the firing stroke. The first sled detent (188A, 188B, 189) positioned on a lateral half of the sled. The second sled detent (188A, 188B, 189) positioned on the lateral half of the sled. Wherein each of the first and second sled detents is configured to independently inhibit the sled from translating distally relative to the jaw prior to the firing stroke.

20 Claims, 24 Drawing Sheets

(56)  References Cited

OTHER PUBLICATIONS

U.S. Appl. No. 18/588,175.
U.S. Appl. No. 18/588,206.
U.S. Appl. No. 18/588,240.
U.S. Appl. No. 18/588,269; and.
U.S. Appl. No. 18/588,684.
U.S. Appl. No. 18/588,094, entitled "Incompatible Staple Cartridge Use Prevention Features for Surgical Stapler," filed Feb. 27, 2024.
U.S. Appl. No. 18/588,147, entitled "Surgical Stapler Cartridge Having Intermediate Raised Tissue Engagement Protrusions," filed Feb. 27, 2024.
U.S. Appl. No. 18/588,175, entitled "Surgical Stapler Cartridge Having Tissue Engagement Protrusions with Enlarged Engagement Surface," filed Feb. 27, 2024.
U.S. Appl. No. 18/588,206, entitled "Surgical Stapler Cartridge Having Raised Surface to Promote Buttress Adhesion," filed Feb. 27, 2024.
U.S. Appl. No. 18/588,240, entitled "Surgical Stapler Cartridge Having Cartridge Retention Features." filed Feb. 27, 2024.
U.S. Appl. No. 18/588,269, entitled "Surgical Stapler Anvil Having Staple Forming Pockets with Laterally Varying Orientations," filed Feb. 27, 2024.
U.S. Appl. No. 18/588,684, entitled "Method of Surgical Stapling," filed Feb. 27, 2024.

* cited by examiner

SLED RETENTION AND ALIGNMENT FEATURES FOR SURGICAL STAPLER

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some instances, a sled of a staple cartridge seated in a jaw of a surgical stapler end effector may inadvertently advance distally before an intended firing stroke, for example when the instrument is mishandled by a user prior to firing such that instrument experiences an impact. Should the sled inadvertently advance distally, it may prematurely eject staples from the staple cartridge, thereby rendering the staple cartridge unusable and potentially also comprising patient tissue still being positioned between the end effector jaws. Therefore, it may be desirable to equip the end effector with a restraining feature to inhibit premature distal advancement of the sled. Known restraining features can be inadequate in that they provide only one longitudinal restrained position of the sled relative to the cartridge body, such that if the restrained position is overcome prior to an intended firing stroke (e.g., by a sudden impact force exerted on the instrument by a user), the sled is free to advance distally and prematurely fire staples. The illustrative restraining features described below cooperate to provide multiple, longitudinally-successive restrained positions of a sled relative to the cartridge body, thereby substantially mitigating the risk of staple ejection before an intended firing stroke.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

Figure 1:
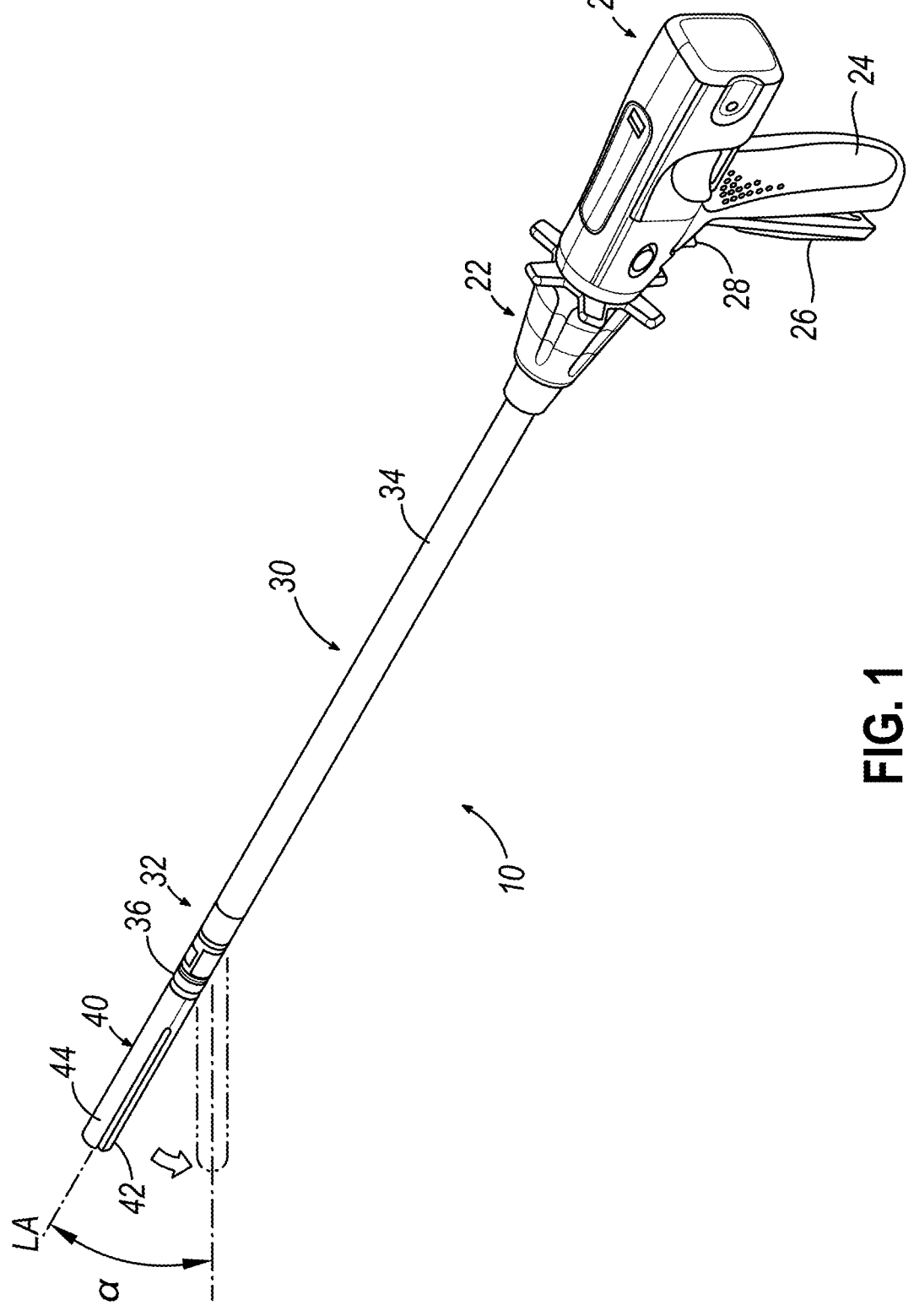
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

I. Illustrative Surgical Stapler

A. Overview of Surgical Stapler Features

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle (a). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
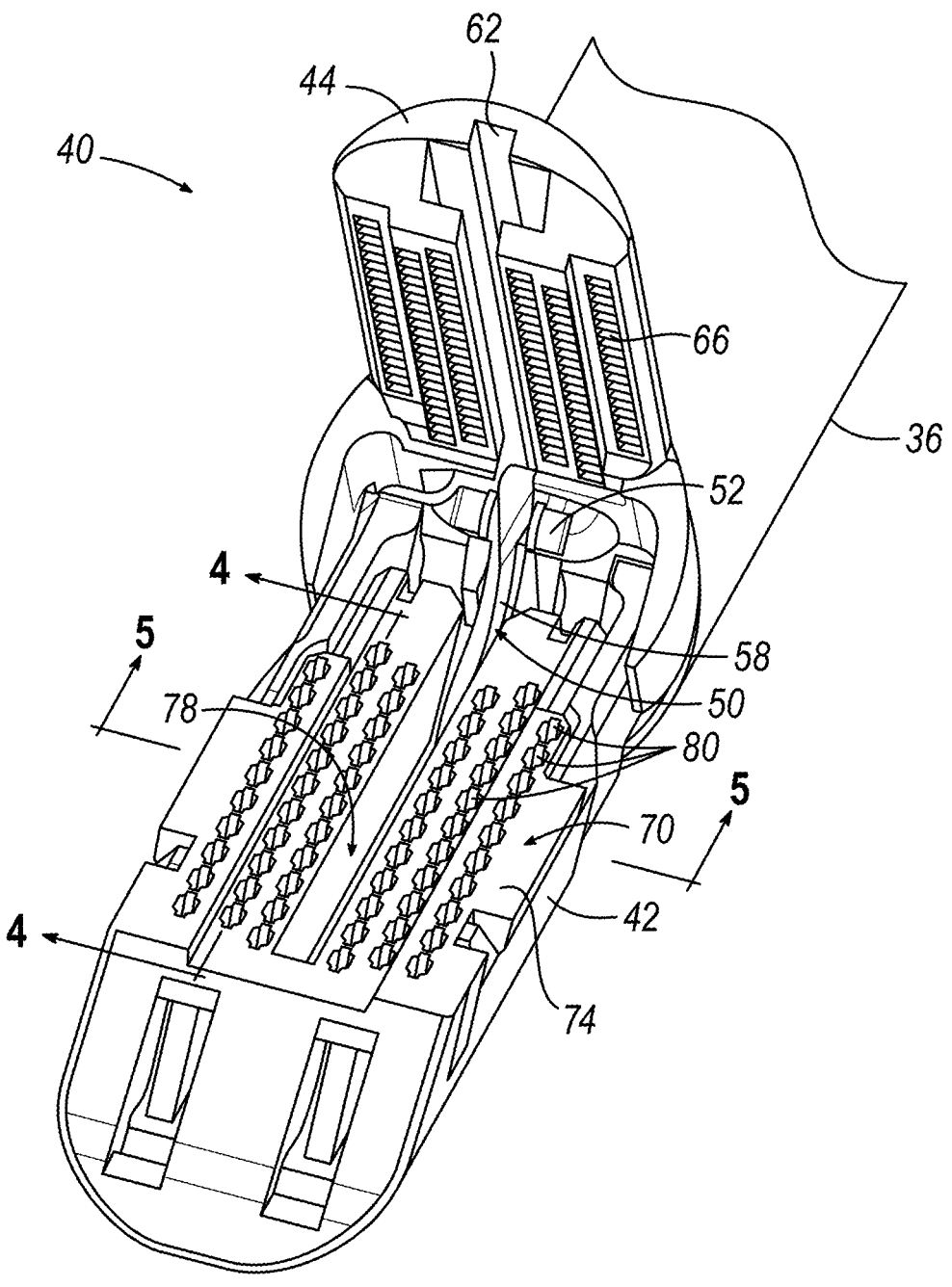
FIG. 2 depicts a perspective view of an end effector of the surgical stapler of FIG. 1, shown in an open state.
Figure 3:
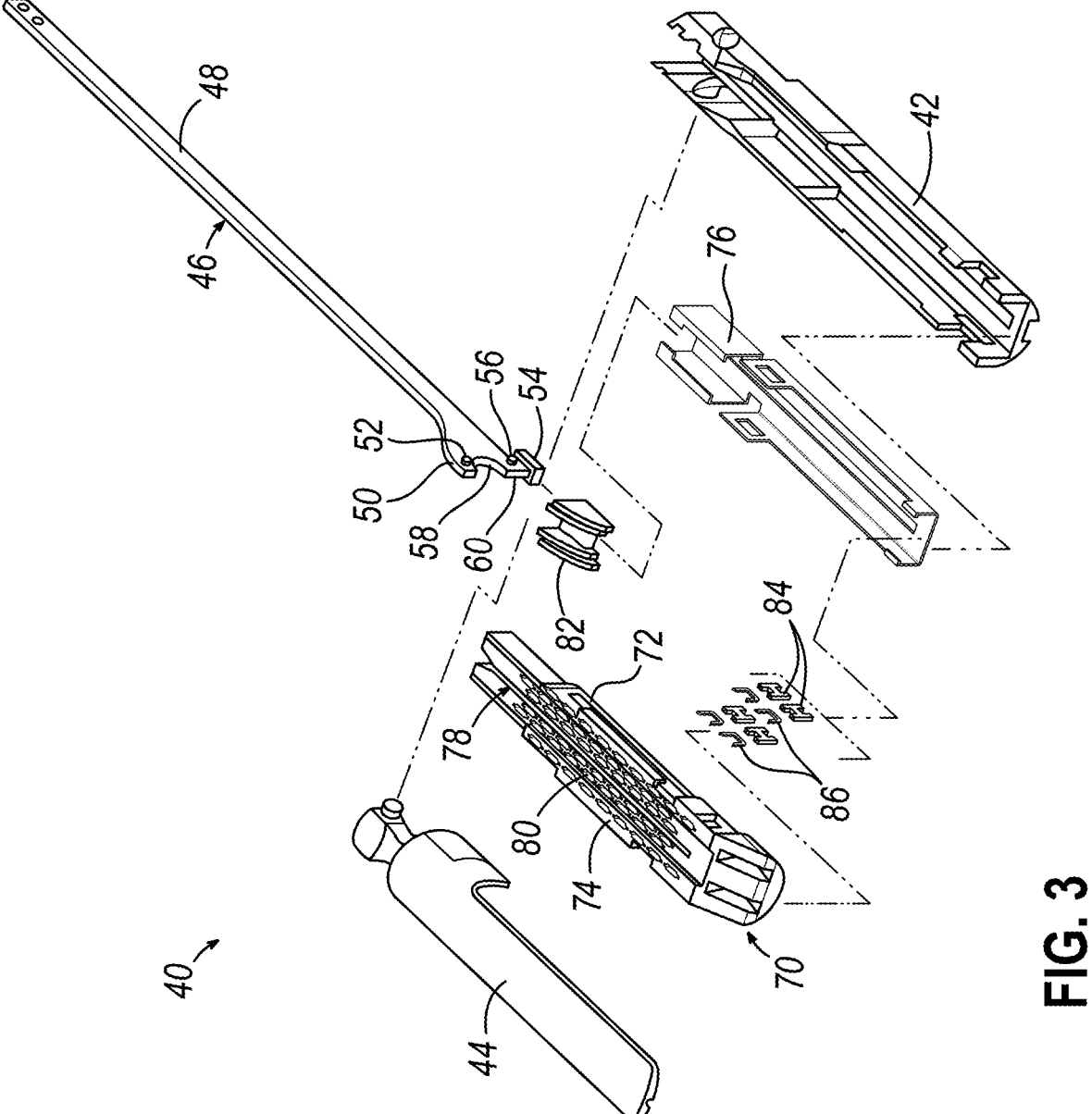
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably seated within a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
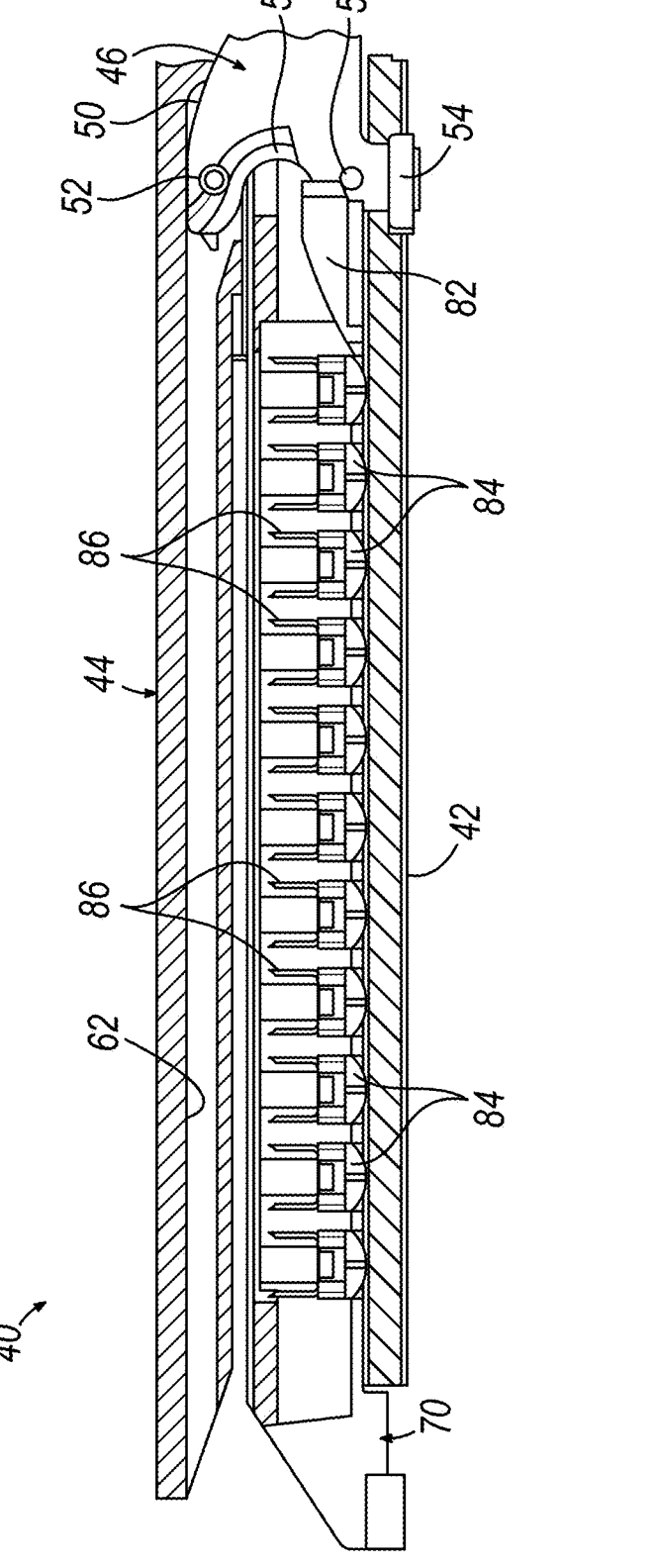
FIG. 4A depicts a side cross-sectional view of the end effector of FIG. 2, taken along line 4-4 of FIG. 2, showing a firing beam and sled in a proximal undisplaced position.
Figure 4B:
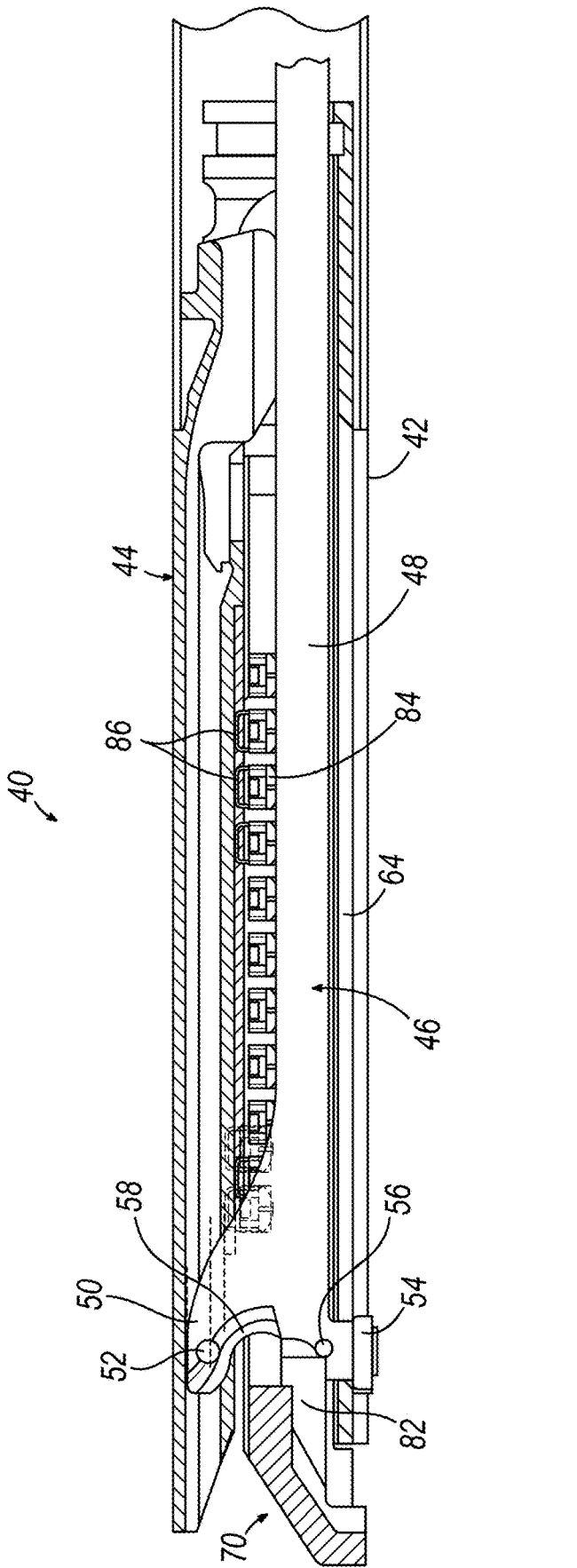
FIG. 4B depicts a side cross-sectional view of the end effector of FIG. 2, taken along line 4-4 of FIG. 2, showing the firing beam and sled in a distal fired position.
Figure 5:
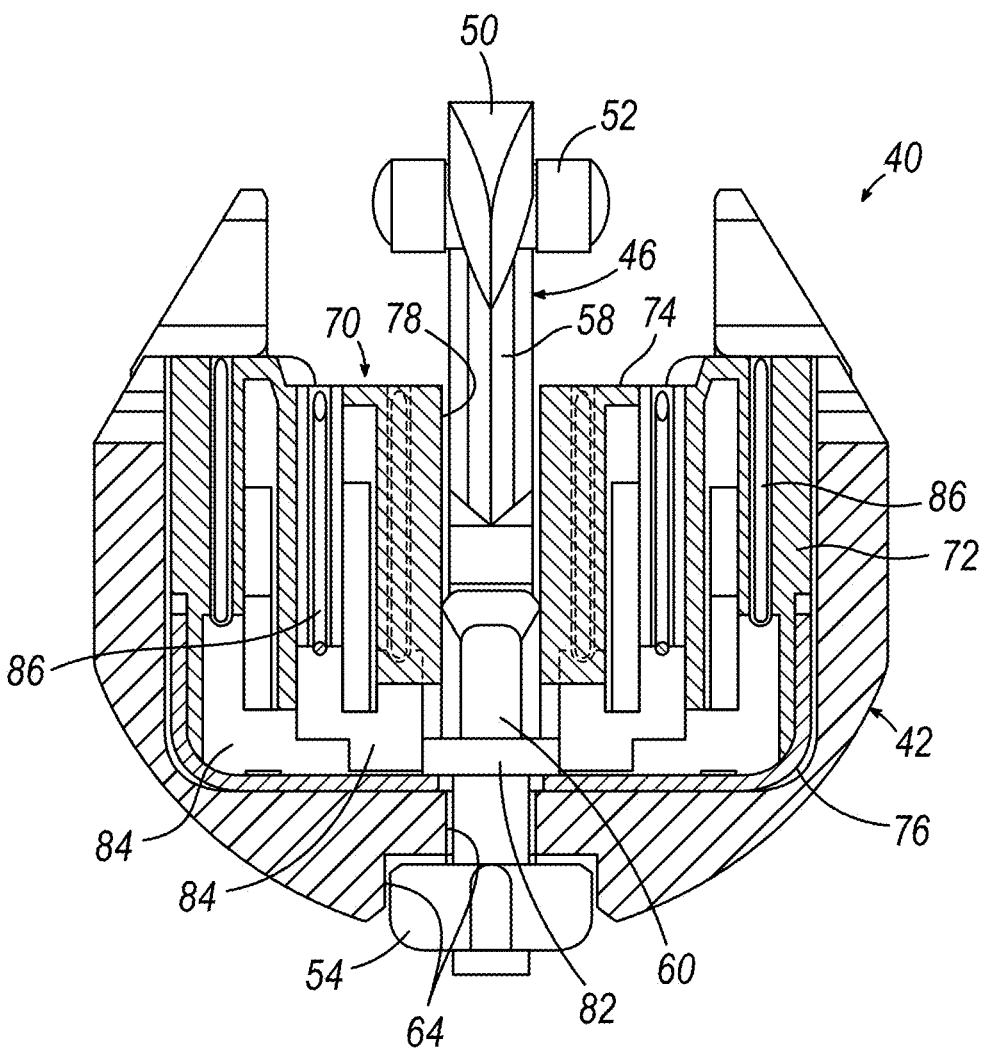
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (43) is aligned with and movable vertically within a respective cartridge pocket (51). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,A248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
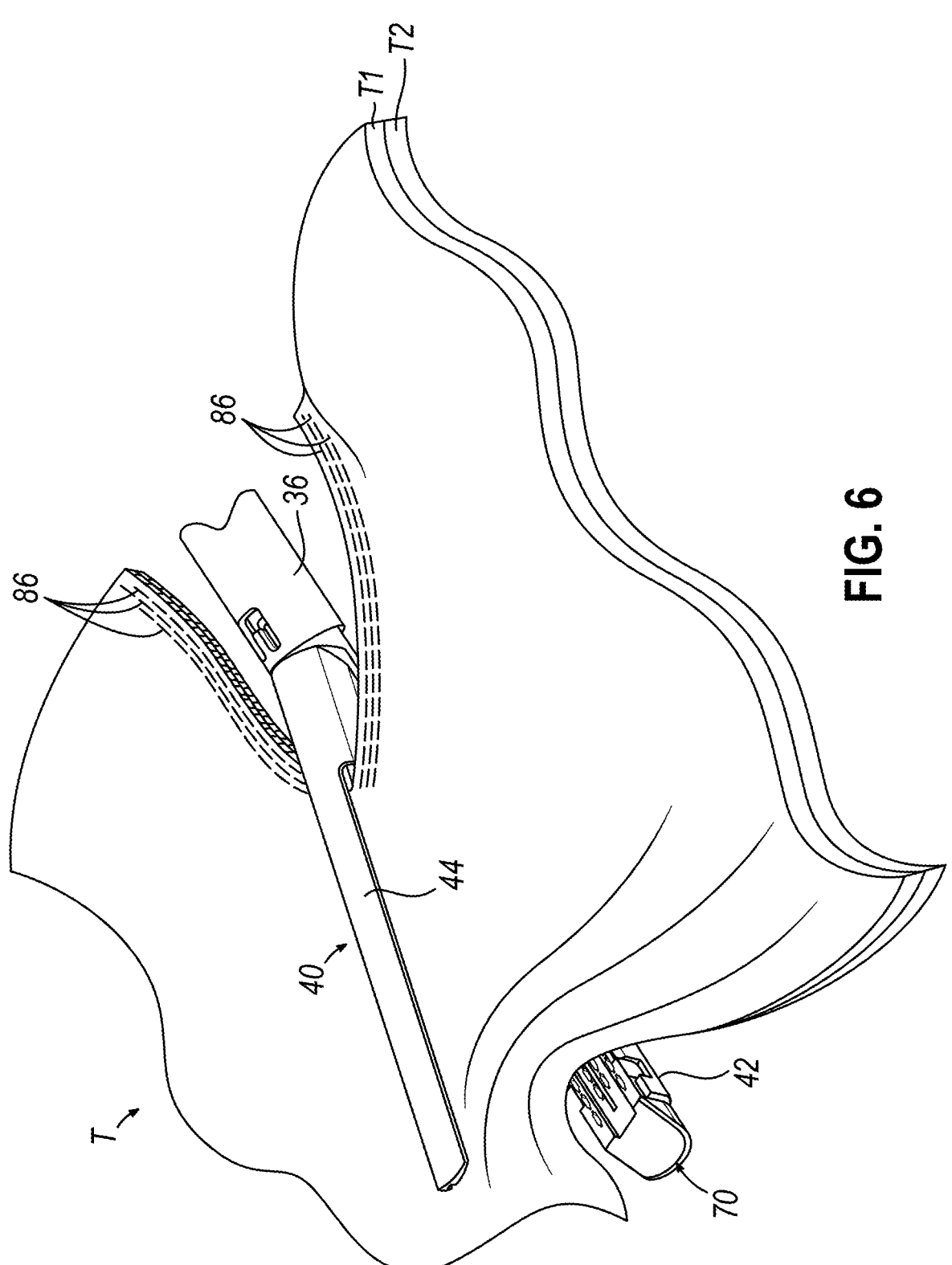
FIG. 6 depicts a perspective view of the end effector of FIG. 3, shown after having been fired once on a first section of tissue and being positioned to clamp and fire on a second section of tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

Surgical stapler (10) described above as well as any of the illustrative surgical stapling features described below may be further configured in accordance with, or otherwise combined with, any of the teachings of U.S. patent application Ser. No. 18/588,684, entitled "Method of Surgical Stapling," filed Feb. 27, 2024, issued as U.S. Pat. No. 12,471,913 on Nov. 18, 2025, the disclosure of which is incorporated by reference herein in its entirety.

B. Illustrative End Effector Sled Restraining Features

As described above, it may be desirable to prevent sled (82) from inadvertently advancing distally during handling of the surgical instrument to protect against premature firing of staples before an intended firing stroke.

Figure 7:
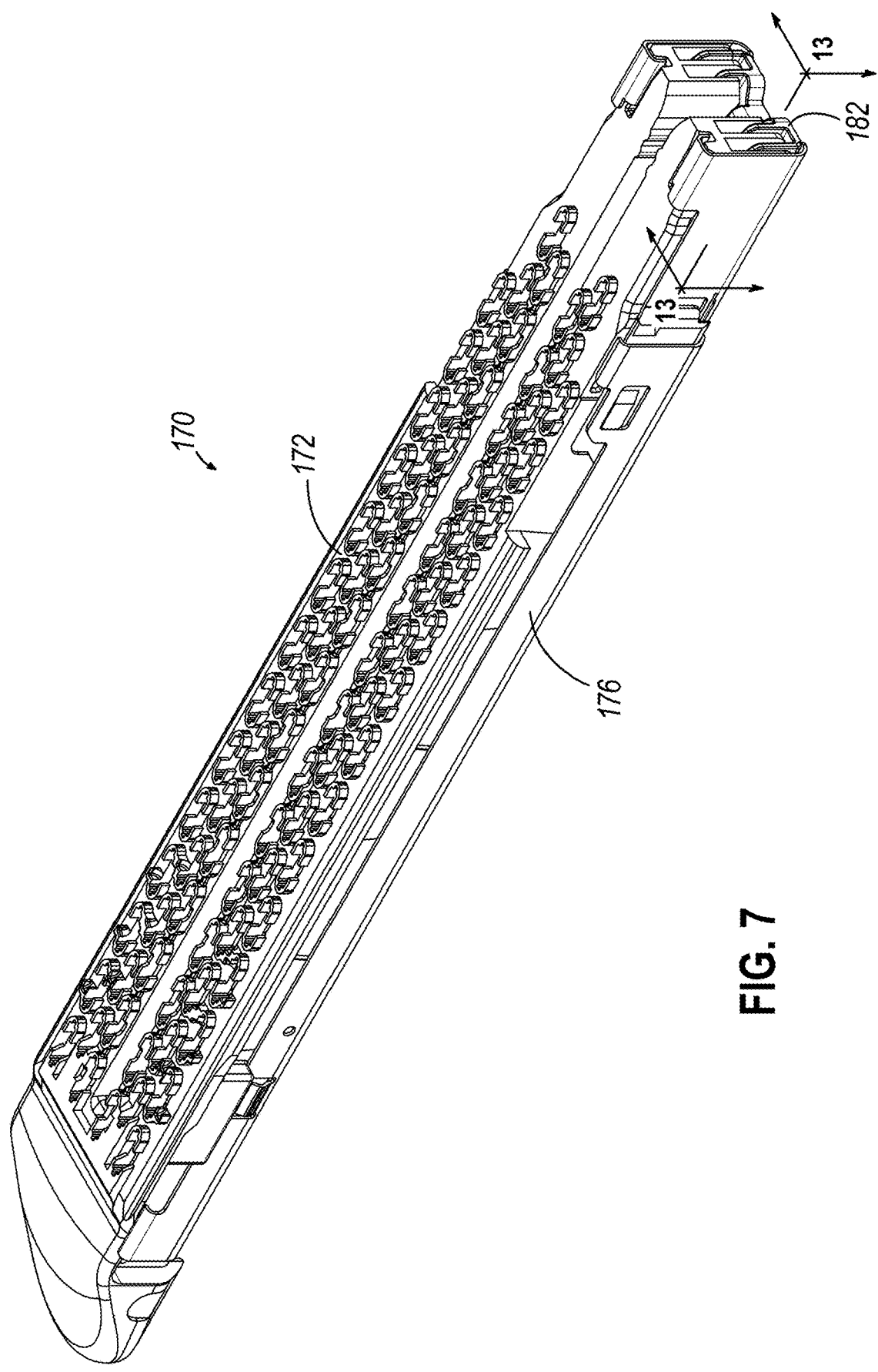
FIG. 7 depicts a perspective view of an alternative staple cartridge having a cartridge body, a sled, and a lower pan.

FIG. 7 shows a portion of another illustrative staple cartridge (170) that may be readily incorporated into end effector (40) of surgical stapler (10) in place of staple cartridge (70). Staple cartridge (170) includes a cartridge body (172), a lower pan (176), and a sled (182), among other features similar to those of staple cartridge (70). As described below, staple cartridge (170) is able to hold or retain sled (182) in place in multiple, longitudinally-successive detented positions to prevent, inhibit, or limit inadvertent translations of sled (182) along staple cartridge (170) and thereby protect against premature firing of staples before an intended firing stroke.

Figure 8:
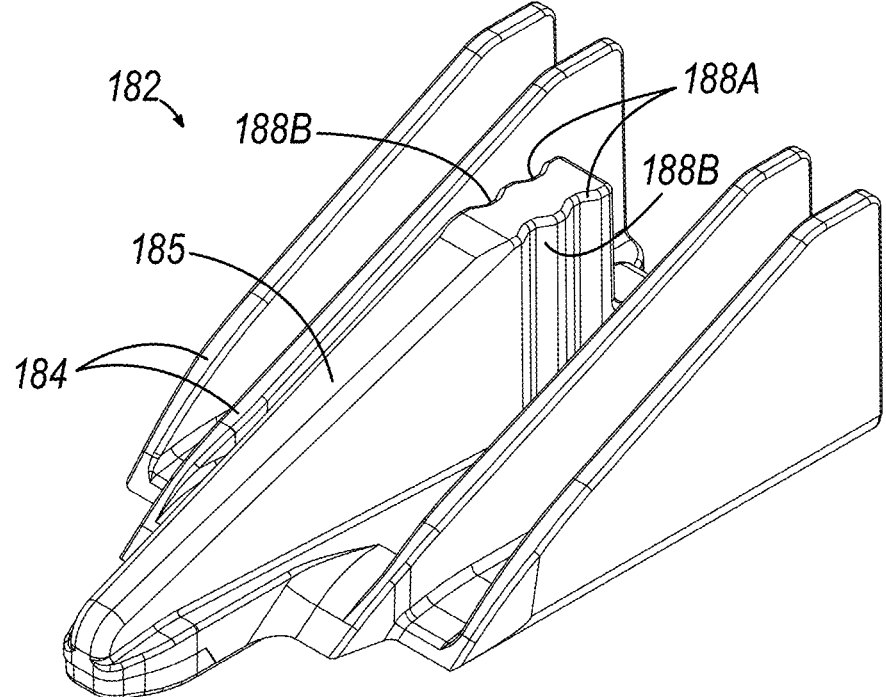
FIG. 8 depicts a top perspective view of a sled of the staple cartridge of FIG. 7, showing having a series of detent recesses along a central rib.

FIG. 8 shows sled (182) including multiple outer rails (184) and a central rail (185) having two pairs of detents (188), shown in the form of vertical grooves. Each pair of detents (188) is positioned on a respective lateral side of central rail (185) and includes a proximal detent (188A) and a distal detent (188B). Each detent (188A, 188B) may have a curved or semicircular profile and may be recessed into the respective lateral side of central rail (185). Detents (188A, 188B) may be positioned anywhere longitudinally along central rail (185) and may extend from an upper edge to a lower edge of central rail (185) or through a portion therein.

Importantly, while detents of sled (182) throughout this illustrative staple cartridge are shown as being openings engaging with corresponding protrusions, their configurations may be reversed. That is to say, what appears as an opening may instead be a protrusion, and any corresponding protrusion may instead be an opening.

Figure 9:
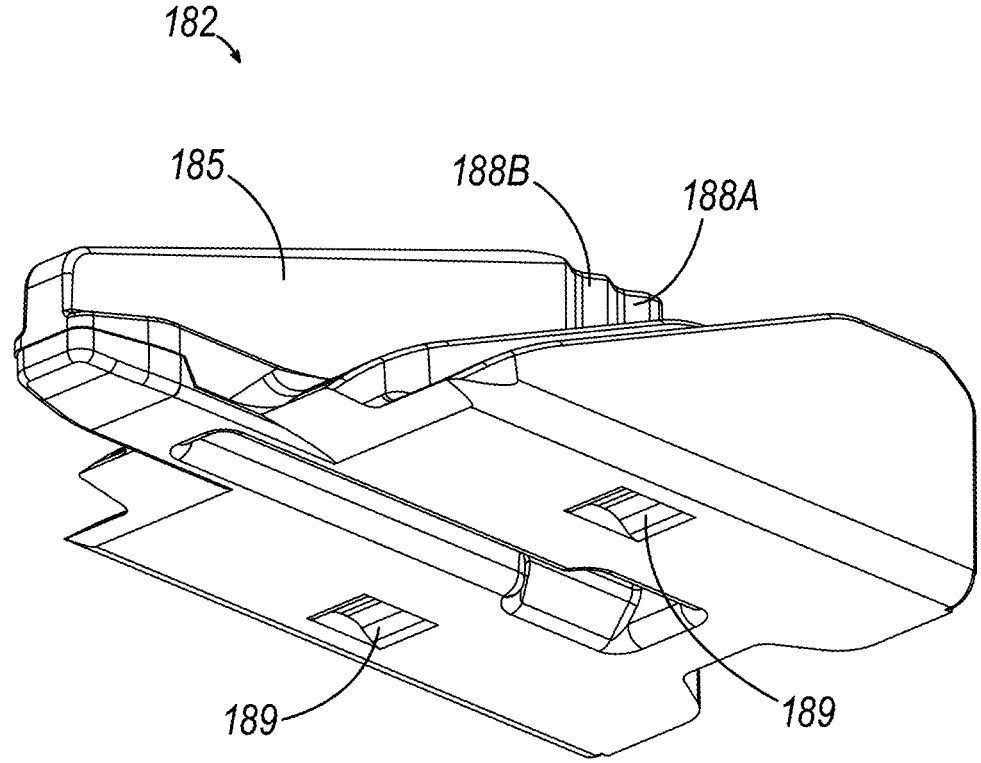
FIG. 9 depicts a bottom perspective view of the sled of FIG. 7, shown having detent recesses along a base.

FIG. 9 shows sled (182) including a pair of base detents (189), shown in the form of recesses, in addition to detents (188). Base detents (189) may be positioned along a bottom surface of sled (182). Base detents (189) may have a curved or semicircular profile having a radius that is perpendicular to the longitudinal direction of sled travel. Base detents (189) may extend through a portion of the bottom of sled (182) and may extend the entire width or a partial width of sled (182). Base detents (189) may be longitudinally aligned with one another and with either of detents (188A, 188B) or may be proximal, distal, or between thereto.

Figure 10:
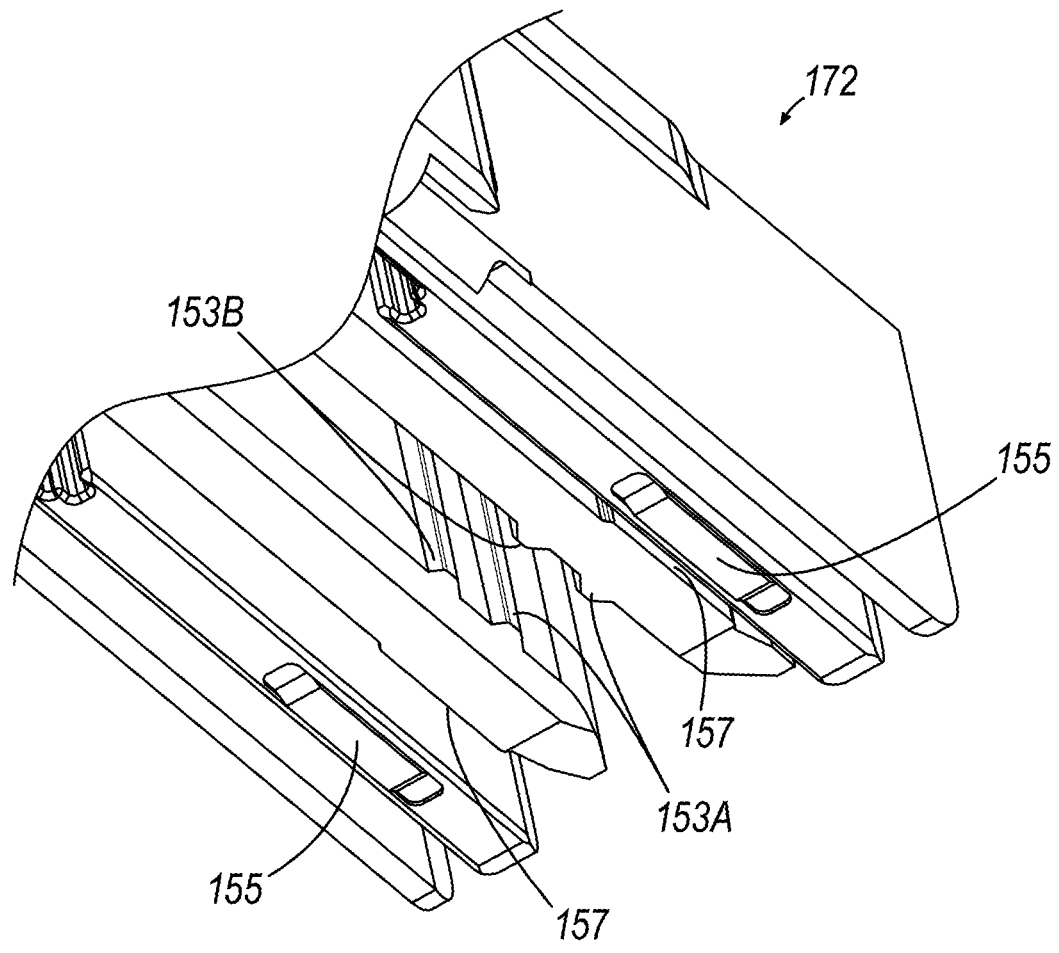
FIG. 10 depicts a bottom perspective view of a proximal portion of the cartridge body of FIG. 7, the cartridge body having multiple pairs of detent protrusions.

FIG. 10 shows a proximal end portion of cartridge body (172) having two pairs of first protrusions (153), each pair of first protrusions (153) including a proximal first protrusion (153A) and a distal first protrusion (153B); a pair of second protrusions (155), and a pair of third protrusions (157). Each of the two pairs of first protrusions (153) project laterally inwardly from a respective vertical inner wall of a longitudinal knife slot of cartridge body (172) and is sized to engage at least one of detents (188A, 188B) on the confronting lateral side of sled (182). This engagement is described in detail below. Each protrusion of the second protrusions (155) extends downwardly and longitudinally along a bottom surface of cartridge body (172) to thereby be positioned between respective outer rails (184). Third protrusions (157) project laterally to thereby engage a respective outer rail (184). Third protrusions (157) may extend from an upper edge to a lower edge of cartridge body (172) or anywhere in between. Each protrusion of the pair of third protrusions (157) is outwardly facing along a channel of cartridge body (172). Alternatively, each protrusion of the pair of third protrusions (157) may be inwardly facing along a channel of cartridge body (172).

Figure 11:
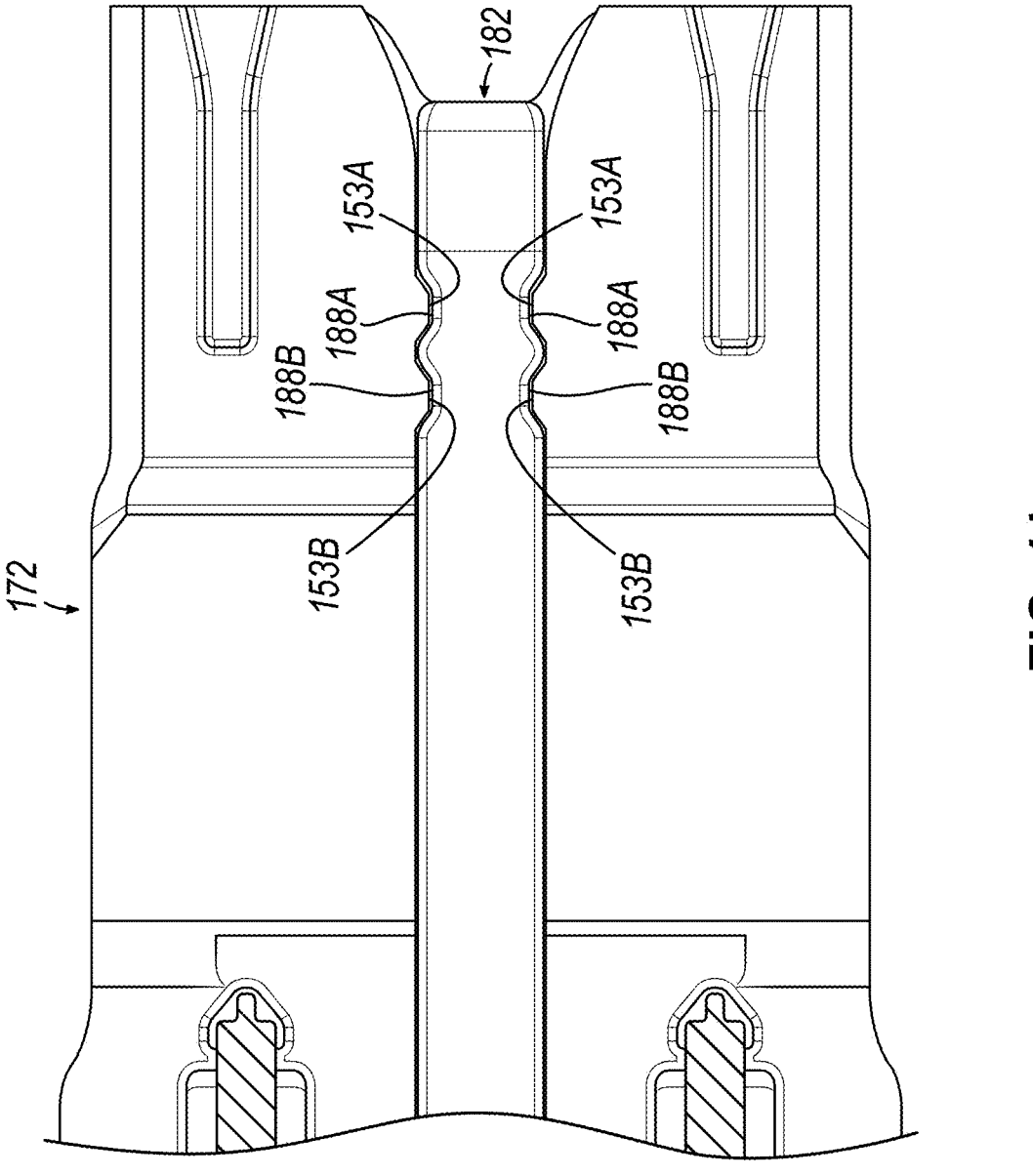
FIG. 11 depicts a top plan view of a proximal end portion of the staple cartridge of FIG. 7, showing the sled engaged with the cartridge body in a first pre-fired position.

FIG. 11 shows sled (182) in a proximal first pre-fired position and engaged with cartridge body (172). With sled (182) in a proximal most position, pair of detents (188) is engaged with pair of first protrusions (153). Specifically, proximal first protrusion (153A) is engaged with proximal detent (188A) and distal first protrusion (153B) is engaged with distal detent (188B) to thereby releasably retain sled (182) in the proximal first pre-fired position.

Figure 12:
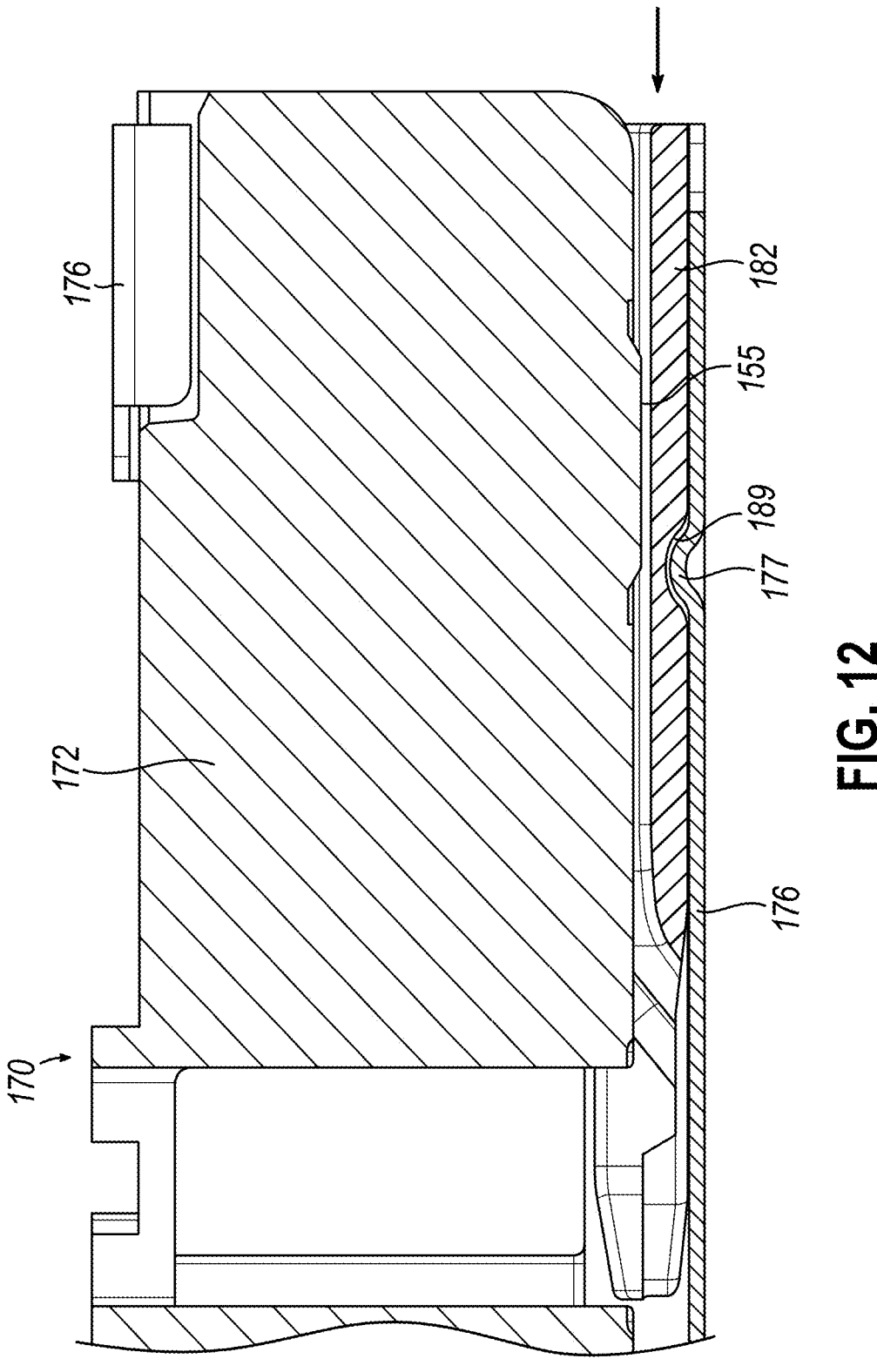
FIG. 12 depicts a cross sectional side view of the proximal end portion of the staple cartridge of FIG. 7, showing the sled in a second pre-fired position.

FIG. 12 shows cartridge body (172), lower pan (176), and sled (182). Sled (182) is shown in a distal second pre-fired position such that detent (189) is engaged with a protrusion (177) of lower pan (176). The distal second pre-fired position of sled (182) is distal to the proximal first pre-fired position. Second protrusions (155) of cartridge body (172) are sized to contact a top surface of sled (182) and thereby press against the top surface of sled (182). As such, second protrusions (155) may increase a force required to disengage detent (189) from protrusion (177). Further, second protrusion (155) may aid in controlling the manufacturing tolerance stack-up between cartridge body (172), lower pan (176), and sled (182) such that there is a controlled gap between cartridge body (172) and lower pan (176) for which sled (182) may translate.

Figure 13A:
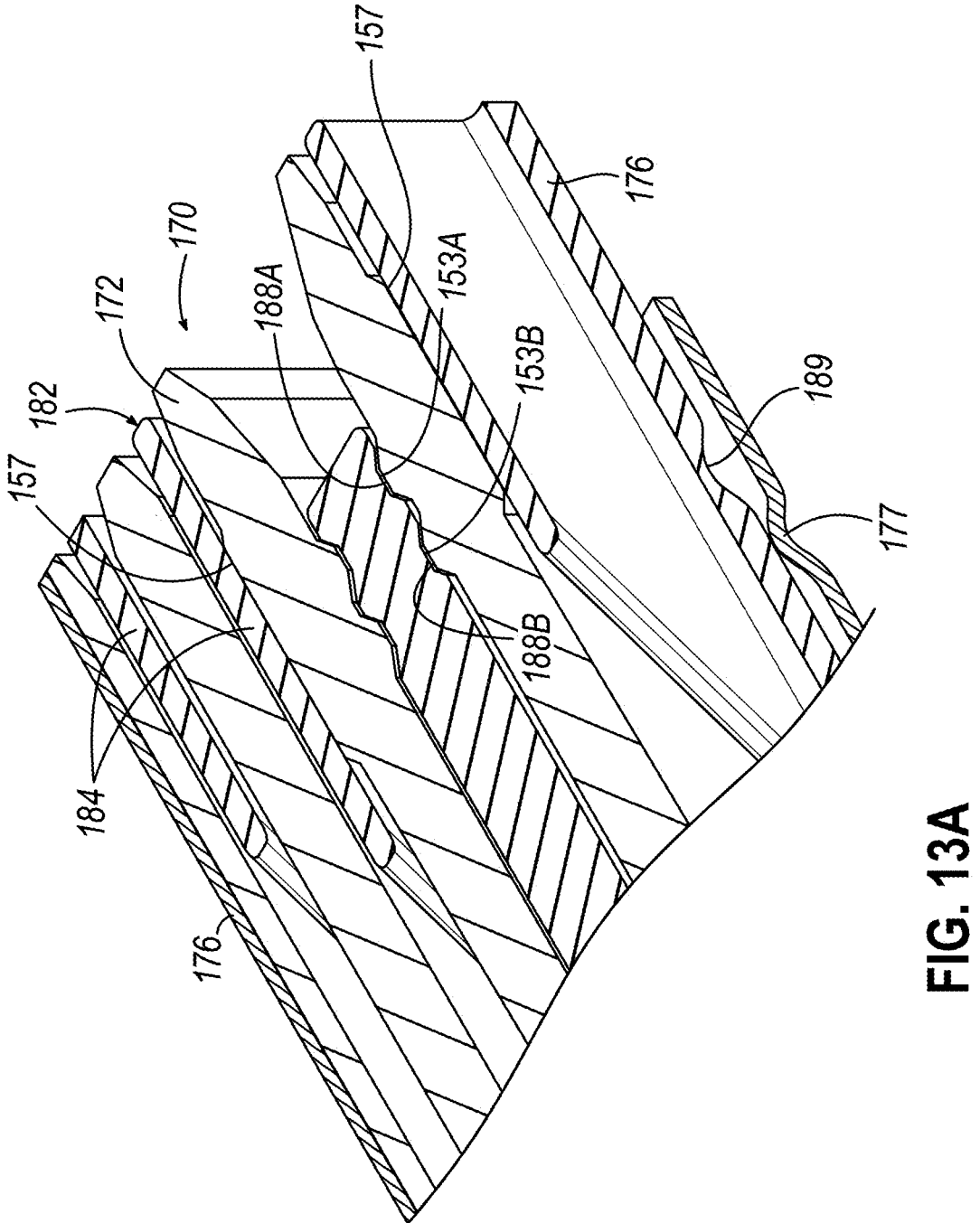
FIG. 13A depicts a cross-sectional view of the proximal end portion of the staple cartridge of FIG. 7, taken along line 13-13 of FIG. 7, showing the sled positioned in the first pre-fired position as shown in FIG. 11.
Figure 13B:
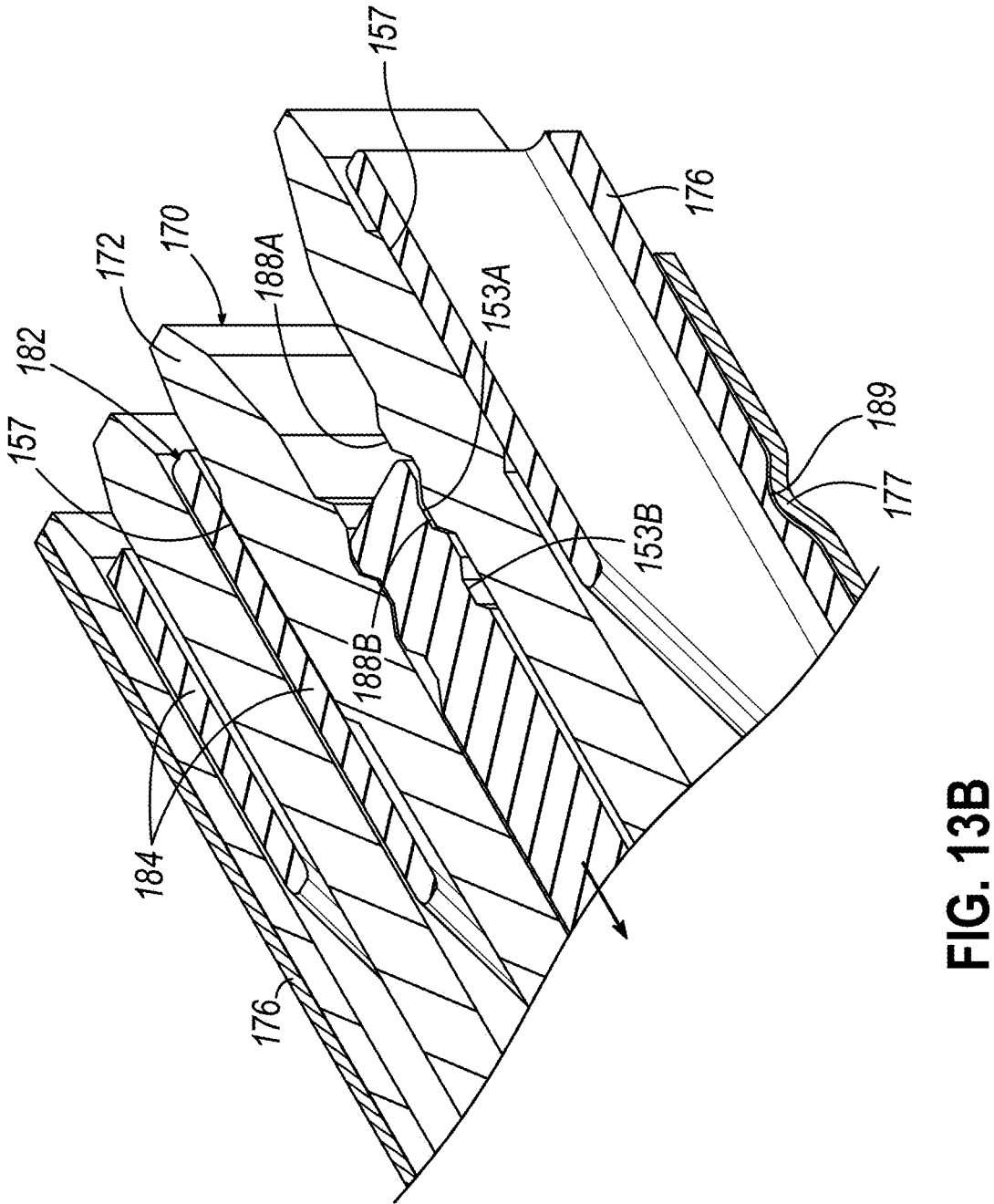
FIG. 13B depicts a cross-sectional view of the cartridge body, lower pan, and sled of FIG. 7, taken along line 13-13 of FIG. 7, showing the sled positioned in a second pre-fired position distal to the first pre-fired position.

FIGS. 13A-13B show sled (182) translating from the proximal first pre-fired position to the distal second pre-fired position. FIG. 13A shows the proximal first pre-fired position of sled (182) where pair of detents (188) is engaged with pair of first protrusions (153) and detent (189) is longitudinally offset from protrusion (177) such that they are disengaged. Optionally, cartridge body (172), lower pan (176), and sled (182) may be absent a respective detent (188A, 188B) of the pair of detents (188), a first protrusion (153A, 153B) of the pair of first protrusions (153), protrusion (177), and/or detent (189).

Third protrusion (157) is shown pressing against sled (182) to thereby constrain sled (182) and to remove any gap or tolerance between the two. Each third protrusion (157) on opposing lateral sides of sled (182) may be used to align central rail (185) of sled (182) centrally within the longitudinal knife slot of cartridge body (172). Doing so may equally distribute holding forces between detent (188) and first protrusions (153), as well as orient sled (182) in a straight orientation such that central rail (185) is inhibited from binding laterally within cartridge body (172). This may be especially important when transitioning between and beyond the first pre-fired position and the second pre-fired position as the laterally opposing first protrusions (153) and detents (188) may be slightly offset from each other during a manufacturing process.

FIG. 13B shows sled (182) in the distal second pre-fired position where sled (182) is advanced to engage distal first protrusion (153B) with proximal detent (188A). Furthermore, base detent (189) is now engaged with protrusion (177) of lower pan (176). As stated above, optionally, sled may be absent proximal detent (188A) or base detent (189) such that one detent (188A, 189) is engaged with a respective protrusion (153B, 177) rather than both when sled (182) is in the second pre-fired position.

In view of the above, it will be appreciated that cartridge body (172), lower pan (176), and sled (182) are structurally configured to provide proximal and distal detented positions of sled (182) relative to cartridge body (172), where sled (182) is configured to be releasably retained in each detented position, successively, to protect against premature distal advancement of sled (182) and resulting premature ejection of staples before an intended firing stroke. The disclosed detent features of staple cartridge (170) may be suitably sized and shaped to engage one another with a detent force sufficient to inhibit premature distal advancement of sled (182) without necessitating an excessive input force for overcoming the detented positions to initiate a firing stroke.

II. Illustrative Features for Interference Fitment Between a Sled and Cartridge Body In certain instances, it may be desirable to create an interference fitment between a sled and a cartridge body of a staple cartridge. An interference fitment may be advantageous to limit backlash (or mechanical play) between the sled and the cartridge body, and to further protect against premature distal movement of the sled before an intended firing stroke. Described below are illustrative features configured to provide such interference fitment between the sled and the cartridge body.

A. Staple Cartridge Having a First Interference Pad

Figure 14:
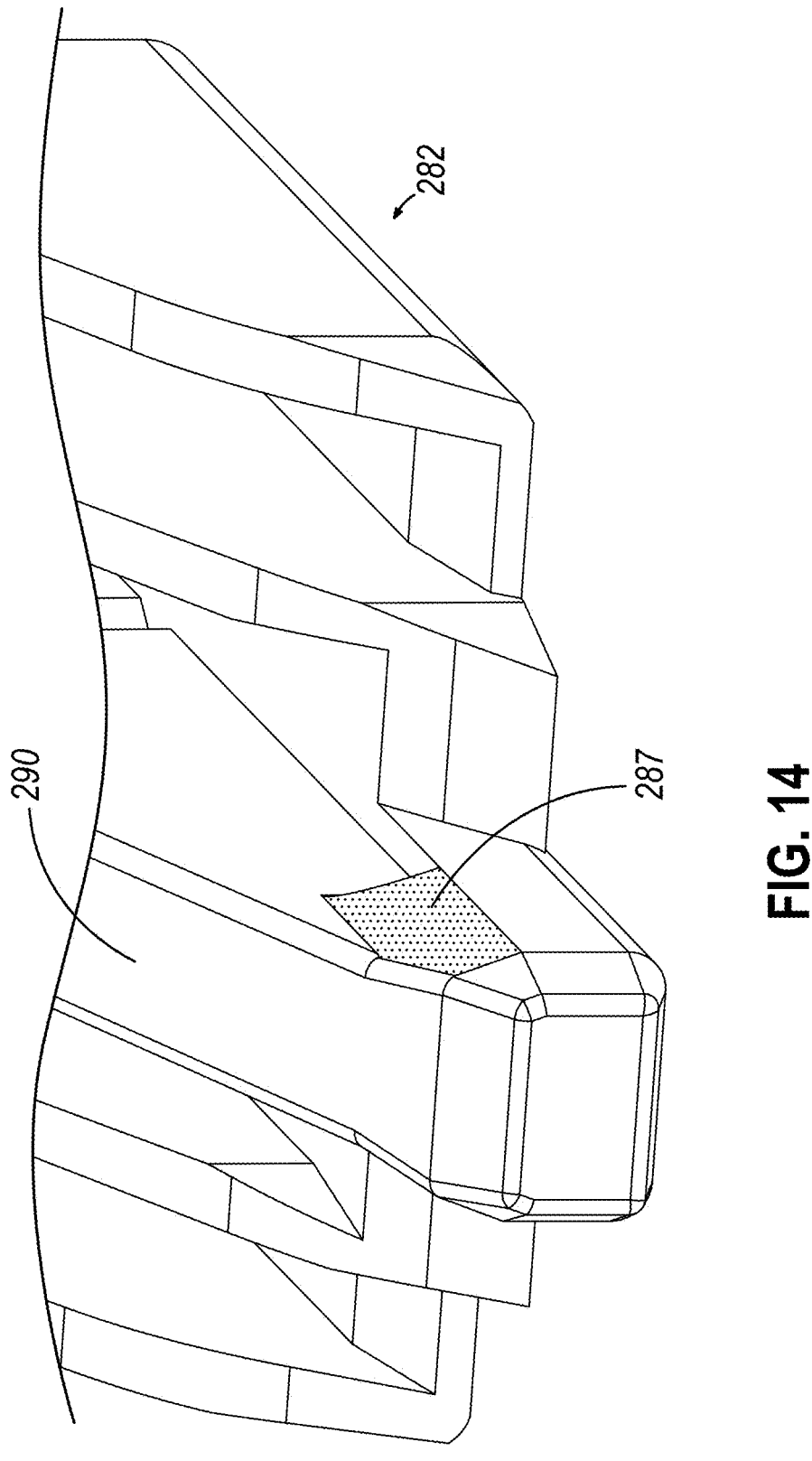
FIG. 14 depicts a front perspective view an alternative sled having a first interference pad.
Figure 15:
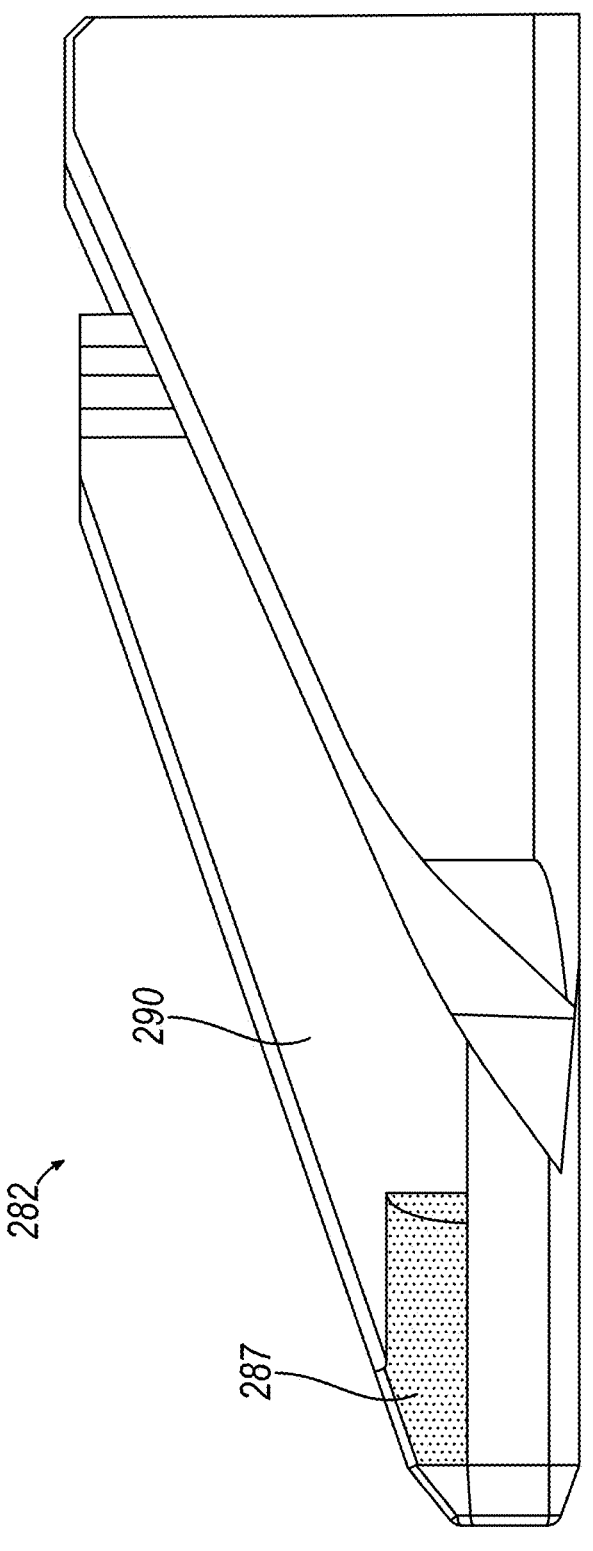
FIG. 15 depicts a side elevational view of the sled of FIG. 14, showing the first interference pad extending along a distal nose.
Figure 16:
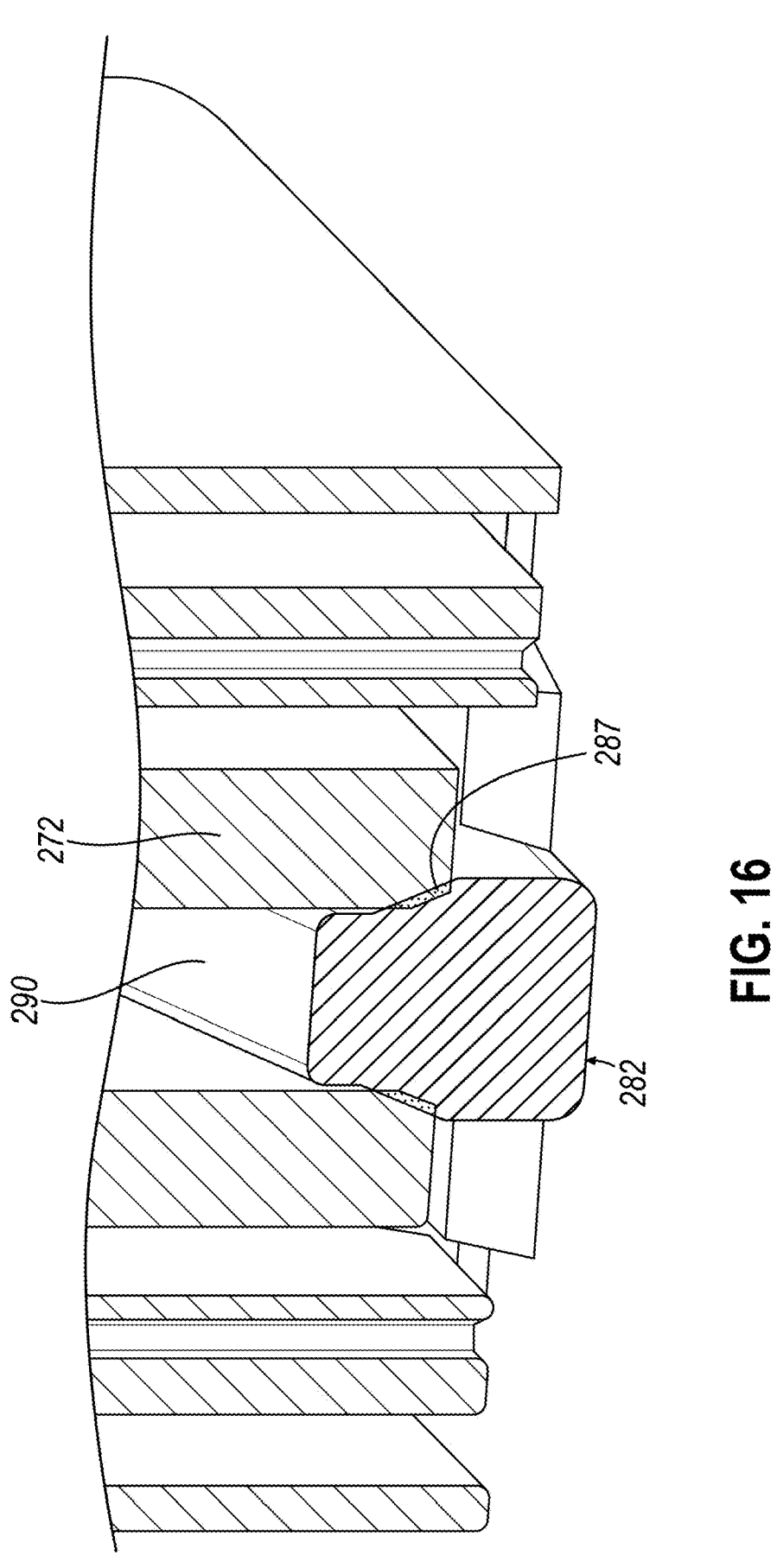
FIG. 16 depicts a front cross-sectional perspective view of the sled of FIG. 14, showing the sled having an interference fitment with an alternative cartridge body.

FIGS. 14-16 show a staple cartridge having a sled (282) with a first interference pad (287) with tapered surfaces on a distal end and a cartridge body (272) having matching interference cutouts. As shown in FIGS. 14-15, first interference pad (287) is positioned on each lateral side of a central rail (290) of sled (282), at a distal end (also referred to as a distal nose) of central rail (290). As shown in FIG. 16, first interference pads (287) are configured to directly contact respective inner walls of a knife slot of cartridge body (272), along the lower edges of the inner walls. Accordingly, first interference pads (287) ensure lateral alignment of the distal nose of sled (282) within the knife slot as sled (282) advances distally through a firing stroke.

B. Staple Cartridge Having a Second Interference Pad

Figure 17:
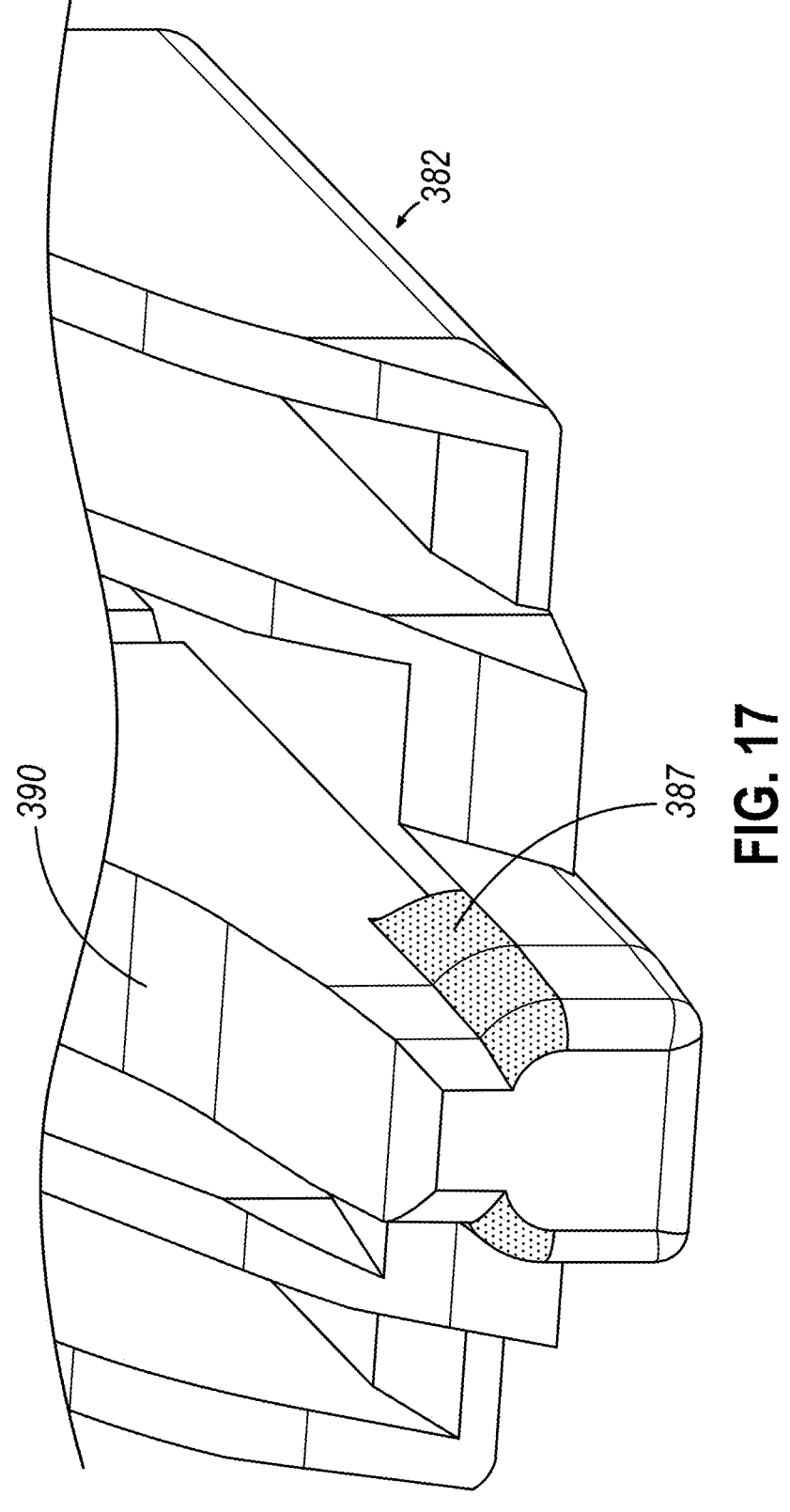
FIG. 17 depicts a front elevational view of an alternative sled having a second interference pad.
Figure 18:
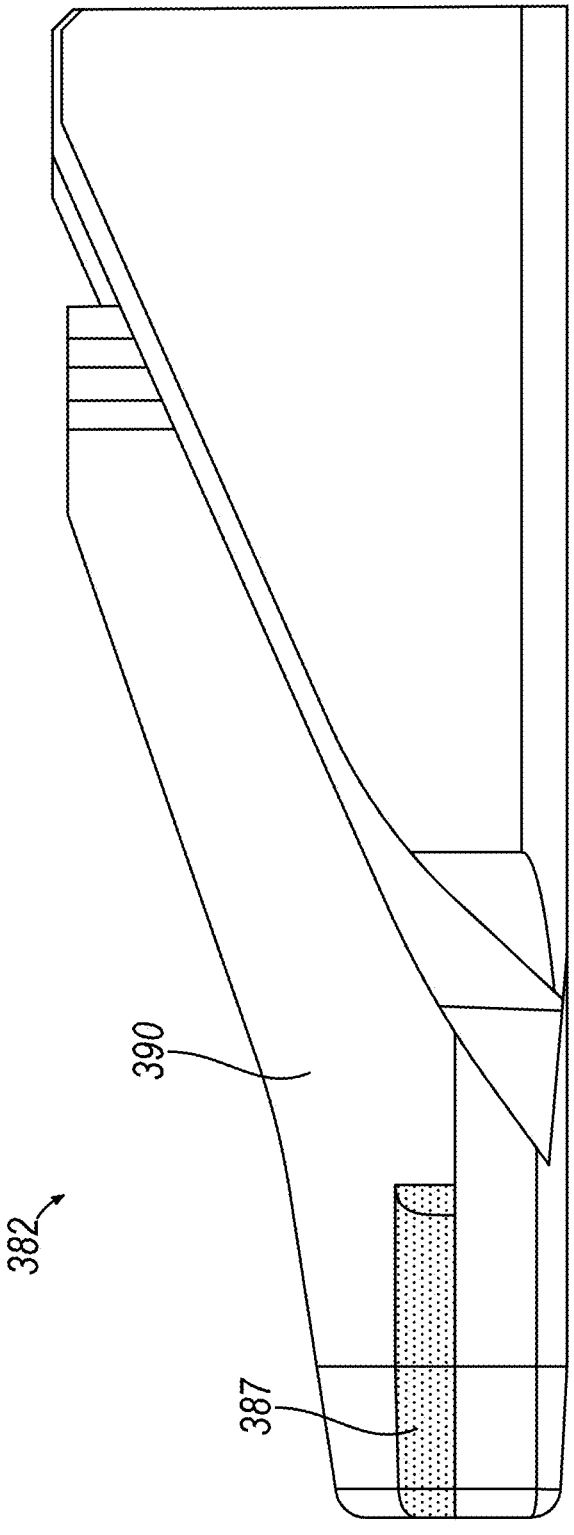
FIG. 18 depicts a side elevational view of the sled of FIG. 17, showing the first interference pad extending along a distal nose.
Figure 19:
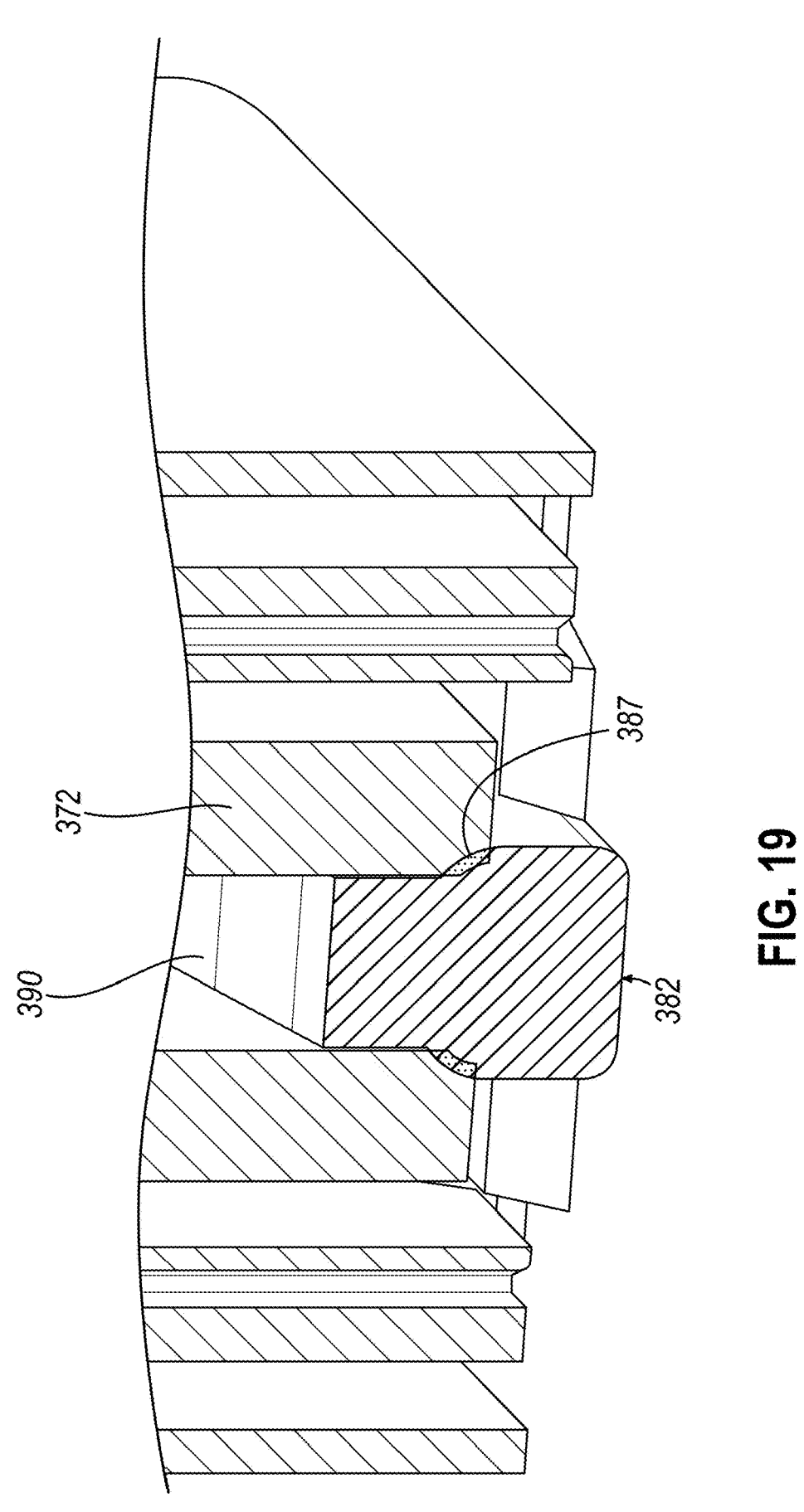
FIG. 19 depicts a front cross-sectional perspective view of the sled of FIG. 17, showing the sled having an interference fitment with an alternative cartridge body.

FIGS. 17-19 show a staple cartridge having a sled (382) with a second interference pad (387) with curved surfaces on a distal end and a cartridge body (372) having matching interference cutouts. As shown in FIGS. 17-18, second interference pad (387) is positioned on each lateral side of a central rail (390) of sled (382), at a distal end (also referred to as a distal nose) of central rail (390). As shown in FIG. 19, first interference pads (387) are configured to directly contact respective inner walls of a knife slot of cartridge body (372), along the lower edges of the inner walls. Accordingly, first interference pads (387) ensure lateral alignment of the distal nose of sled (382) within the knife slot as sled (382) advances distally through a firing stroke.

C. Staple Cartridge Having a Third Interference Pad

Figure 20:
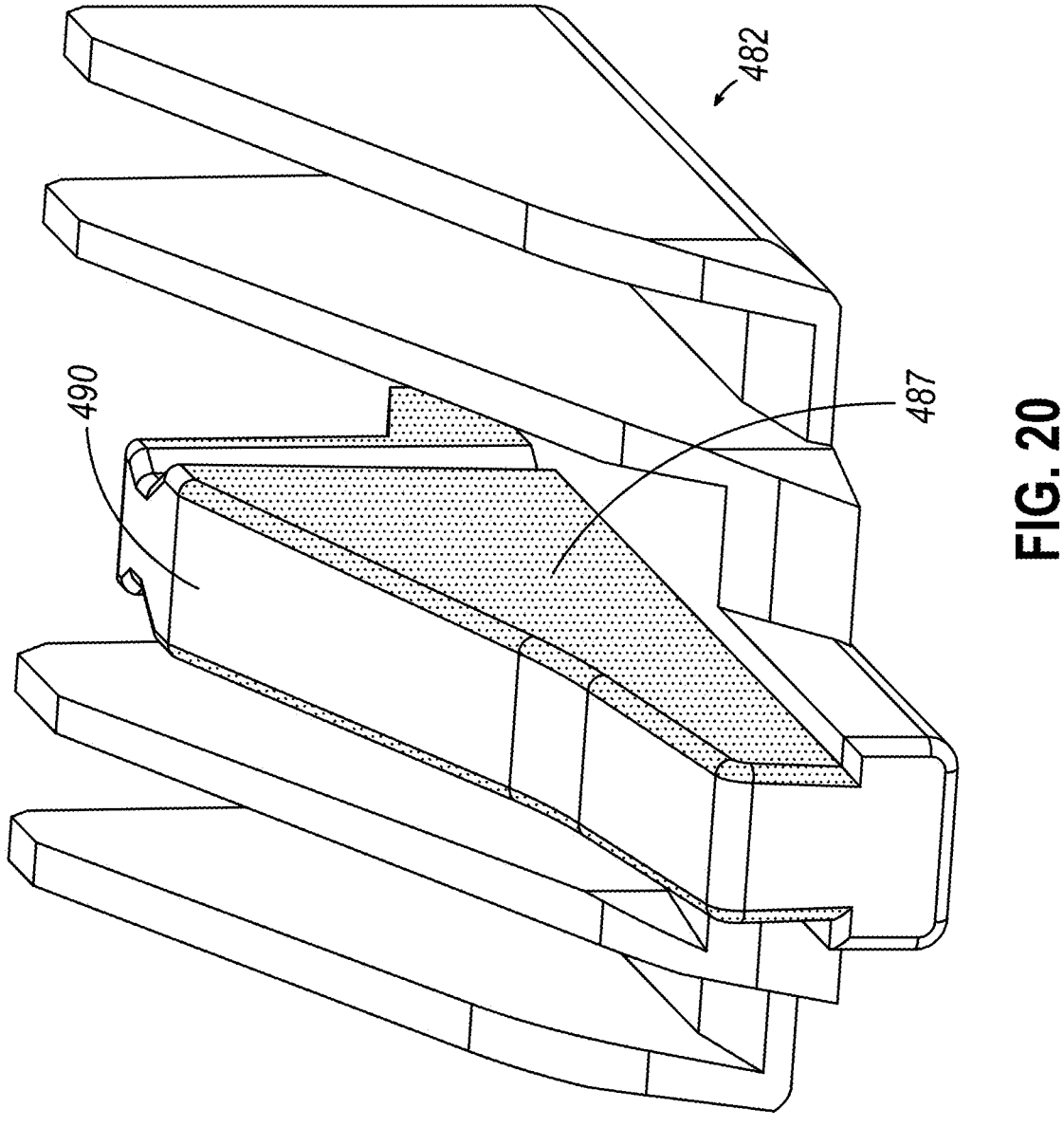
FIG. 20 depicts a front perspective view of an alternative sled having a third interference pad.
Figure 21:
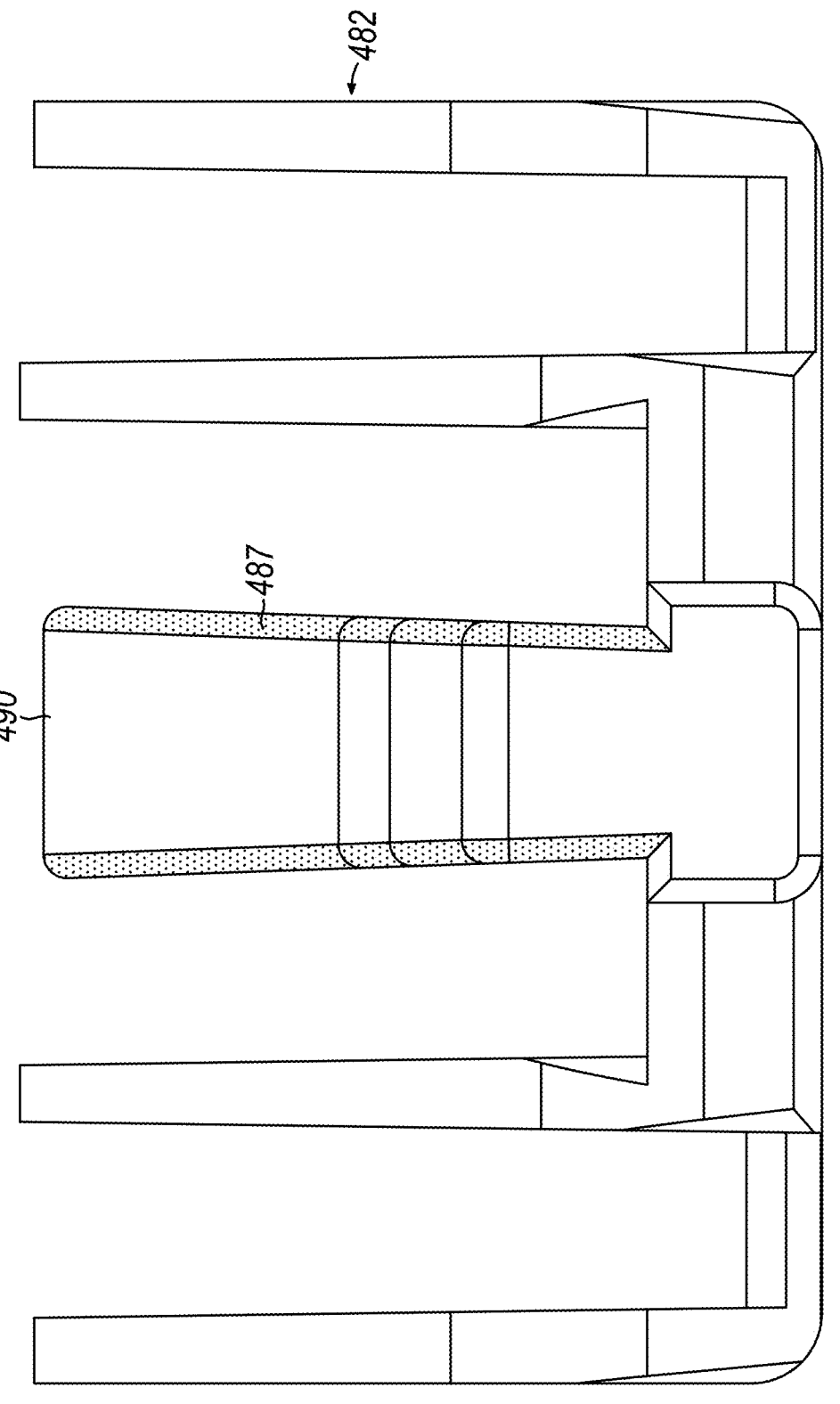
FIG. 21 depicts a side elevational view of the sled of FIG. 20, showing the third interference pad extending along a central rib.
Figure 22:
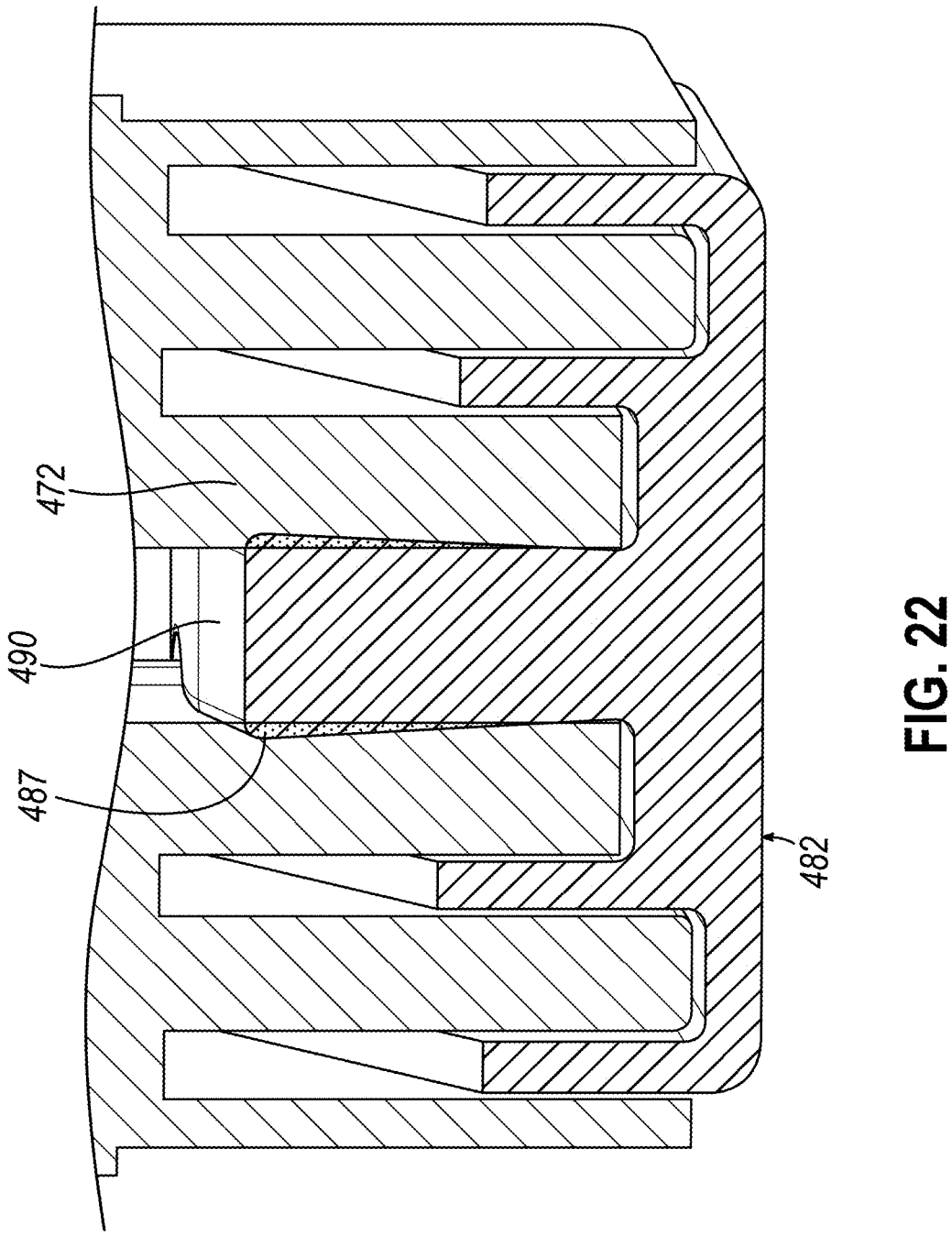
FIG. 22 depicts a front cross-sectional perspective view of the sled of FIG. 20, showing the sled having an interference fitment with an alternative cartridge body.

FIGS. 20-22 show a staple cartridge having a sled (482) with a third interference pad (487) with angled surfaces along a center rail (490) and a cartridge body (472). As shown in FIGS. 20-21, third interference pad (487) is positioned on each lateral side of central rail (490) of sled (482). As shown in FIG. 22, third interference pads (487) are configured to directly contact respective inner walls of a knife slot of cartridge body (472), along the lower edges of the inner walls. Accordingly, third interference pads (487) ensure lateral alignment of the central rail (490) of sled (482) within the knife slot as sled (482) advances distally through a firing stroke.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

1. A sled (182) for a surgical stapler, the sled comprising:
   (a) a base configured to translate distally relative to a jaw of the surgical stapler through a firing stroke to eject a plurality of staples into tissue;
   (b) a plurality of rails (184, 185) extending upwardly from the base and configured to guide distal translation of the sled within the jaw through the firing stroke;
   (c) a first sled detent (188A, 188B, 189) positioned on a lateral half of the sled; and
   (d) a second sled detent (188A, 188B, 189) positioned on the lateral half of the sled,
   wherein each of the first and second sled detents is configured to independently inhibit the sled from translating distally relative to the jaw prior to the firing stroke.

Example 2

2. The sled of example 1, wherein the first sled detent is configured to releasably retain the sled in a first pre-fired position and the second sled detent is configured to releasably retain the sled in a second pre-fired position distal to the first pre-fired position.

Example 3

3. The sled as in any one of the preceding examples, wherein the first sled detent comprises one of a detent protrusion or a detent opening configured to releasably engage the other of a detent protrusion or a detent opening to inhibit distal translation of the sled, and wherein the second sled detent comprises a second detent protrusion or a second detent opening configured to releasably engage the other of a detent protrusion or a detent opening to inhibit distal translation of the sled independently from the first sled detent.

Example 4

4. The sled as in any one of the preceding examples, wherein the plurality of rails defines at least one of the first sled detent or the second sled detent.

Example 5

5. The sled as in any one of the preceding examples, wherein the base defines the first sled detent and a rail of the plurality of rails defines the second sled detent.

Example 6

6. The sled as in one of examples 1-4, wherein the plurality of rails defines the first sled detent and the second sled detent.

Example 7

7. The sled as in any one of the preceding examples, wherein the first and second sled detents are configured to engage respective protrusions of a staple cartridge body upon a distal translation of the sled relative to the staple cartridge body.

Example 8

8. The sled as in any one of the preceding examples, wherein the first sled detent is positioned distal to the second sled detent.

Example 9

9. The sled as in any of examples 1~4 or 5-8, wherein the first sled detent and the second sled detent are configured to engage a first protrusion (153A, 153B) and a second protrusion (153A, 153B), respectively, of a staple cartridge body (172) to thereby inhibit distal translation of the sled relative to the staple cartridge body.

Example 10

10. The sled as in any of examples 1~4 or 5-9, wherein each of the first detent and the second detent is positioned along a tallest portion of the sled.

Example 11

11. A surgical staple cartridge, comprising:
   (a) a cartridge body (172) that houses a plurality of staples;
   (b) a cartridge pan (176) that encloses at least a portion of an underside of the cartridge body;
   (c) the sled as in any one of the preceding examples, wherein the sled is slidably disposed between the cartridge body and the cartridge pan; and
   (d) a mating detent (153A, 153B, 177) defined by one of the cartridge body or the cartridge pan and configured to releasably engage at least one of the first sled detent or the second sled detent to inhibit distal translation of the sled relative to the cartridge body prior to the firing stroke.

Example 12

12. The surgical staple cartridge of example 11, wherein the mating detent comprises a first mating detent and is configured to releasably engage the first sled detent to inhibit distal translation of the sled, further comprising a second mating detent longitudinally offset from the first mating detent and configured to releasably engage the second sled detent to inhibit distal translation of the sled independently from the first sled detent and the first mating detent.

Example 13

13. The surgical staple cartridge of example 12, wherein the first and second sled detents are spaced apart by a first longitudinal distance and the first and second mating detents are spaced apart by a second longitudinal distance that is unequal to the first longitudinal distance such that the first sled detent and the first mating detent are configured to engage one another while the second sled detent and the second mating detent are disengaged from one another and such that the second sled detent and the second mating detent are configured to engage one another while the first sled detent and the first mating detent are disengaged from one another.

Example 14

14. The surgical staple cartridge of example 12, wherein the first and second sled detents are spaced apart by a longitudinal distance and the first and second mating detents are also spaced apart by the longitudinal distance such that first sled detent and the first mating detent are configured to engage one another while the second sled detent and the second mating detent engage one another.

Example 15

15. The surgical staple cartridge of example 12, wherein the cartridge body defines one of the first mating detent or the second mating detent and the cartridge pan defines the other of the first mating detent or the second mating detent.

Example 16

16. A staple cartridge (170) configured to be at least partially seated within a cartridge jaw of a surgical stapler, wherein the staple cartridge includes:
   (a) a staple cartridge body (172); and
   (b) a sled (182) slidably coupled with the staple cartridge body and drivable distally from a proximal undisplaced position to deploy staples from the staple cartridge body, wherein the sled includes a first detent (188A, 188B, 189) and a second detent (188A, 188B, 189), wherein each of the first and second detents is configured to inhibit the sled from translating relative to the staple cartridge body, wherein the first detent and the second detent are axially aligned with one another parallel to a longitudinal axis of the staple cartridge.

Example 17

17. The staple cartridge of example 16, wherein each of the first detent and the second detent includes a profile extending along a length of each of the respective first and second detents.

Example 18

18. The staple cartridge as in any one of examples 16 and 17, wherein each of the first and second detents is configured to engage respective protrusions of the staple cartridge body upon a distal translation of the sled relative to the staple cartridge body.

Example 19

19. The staple cartridge as in any one of examples 16, 17, and 18, wherein the first detent and the second detent are configured to engage the staple cartridge body in a proximal-most position of the sled relative to the staple cartridge body.

Example 20

20. A method of inhibiting premature firing of a surgical staple cartridge (170) having a cartridge body (172), a cartridge sled (182) actuatable distally through the cartridge body to eject staples, and a cartridge pan, the method comprising:

(a) engaging the cartridge sled with a first mating detent (153A, 153B, 177) defined by one of the cartridge body or the cartridge pan to releasably retain the cartridge sled in a first longitudinal position;

(b) permitting the sled to translate distally from the first longitudinal position such that the cartridge sled disengages the first mating detent; and (c) engaging the cartridge sled with a second mating detent (153A, 153B, 177) defined by one of the cartridge body or the cartridge pan to releasably retain the cartridge sled in a second longitudinal position distal to the first longitudinal position.

The following clauses also relate to various non-exhaustive ways in which the teachings herein may be combined or applied.

Clause 1

1. A sled for a surgical stapler, the sled comprising:

(a) a base configured to translate distally relative to a jaw of the surgical stapler through a firing stroke to eject a plurality of staples into tissue;

(b) a plurality of rails extending upwardly from the base and configured to guide distal translation of the sled within the jaw through the firing stroke;

(c) a first sled detent positioned on a lateral half of the sled; and (d) a second sled detent positioned on the lateral half of the sled, wherein each of the first and second sled detents is configured to independently inhibit the sled from translating distally relative to the jaw prior to the firing stroke.

Clause 2

2. The sled of clause 1, wherein the first sled detent is configured to releasably retain the sled in a first pre-fired position and the second sled detent is configured to releasably retain the sled in a second pre-fired position distal to the first pre-fired position.

Clause 3

3. The sled of clause 1, wherein the first sled detent comprises one of a detent protrusion or a detent opening configured to releasably engage the other of a detent protrusion or a detent opening to inhibit distal translation of the sled, and wherein the second sled detent comprises a second detent protrusion or a second detent opening configured to releasably engage the other of a detent protrusion or a detent opening to inhibit distal translation of the sled independently from the first sled detent.

Clause 4

4. The sled of clause 1, wherein the plurality of rails defines at least one of the first sled detent or the second sled detent.

Clause 5

5. The sled of clause 1, wherein the base defines the first sled detent and a rail of the plurality of rails defines the second sled detent.

Clause 6

6. The sled of clause 1, wherein the plurality of rails defines the first sled detent and the second sled detent.

Clause 7

7. The sled of clause 1, wherein the first and second sled detents are configured to engage respective protrusions of a staple cartridge body upon a distal translation of the sled relative to the staple cartridge body.

Clause 8

8. The sled of clause 7, wherein the first sled detent is positioned distal to the second sled detent.

Clause 9

9. The sled of clause 1, wherein the first sled detent and the second sled detent are configured to engage a first protrusion and a second protrusion, respectively, of a staple cartridge body to thereby inhibit distal translation of the sled relative to the staple cartridge body.

Clause 10

10. The sled of clause 1, wherein each of the first detent and the second detent is positioned along a tallest portion of the sled.

Clause 11

11. A surgical staple cartridge, comprising:

(a) a cartridge body that houses a plurality of staples;

(b) a cartridge pan that encloses at least a portion of an underside of the cartridge body;

(c) the sled of clause 1, wherein the sled is slidably disposed between the cartridge body and the cartridge pan; and (d) a mating detent defined by one of the cartridge body or the cartridge pan and configured to releasably engage at least one of the first sled detent or the second sled detent to inhibit distal translation of the sled relative to the cartridge body prior to the firing stroke.

Clause 12

12. The surgical staple cartridge of clause 11, wherein the mating detent comprises a first mating detent and is configured to releasably engage the first sled detent to inhibit distal translation of the sled, further comprising a second mating detent longitudinally offset from the first mating detent and configured to releasably engage the second sled detent to inhibit distal translation of the sled independently from the first sled detent and the first mating detent.

Clause 13

13. The surgical staple cartridge of clause 12, wherein the first and second sled detents are spaced apart by a first longitudinal distance and the first and second mating detents are spaced apart by a second longitudinal distance that is unequal to the first longitudinal distance such that the first sled detent and the first mating detent are configured to engage one another while the second sled detent and the second mating detent are disengaged from one another and such that the second sled detent and the second mating detent are configured to engage one another while the first sled detent and the first mating detent are disengaged from one another.

Clause 14

14. The surgical staple cartridge of clause 12, wherein the first and second sled detents are spaced apart by a longitudinal distance and the first and second mating detents are also spaced apart by the longitudinal distance such that first sled detent and the first mating detent are configured to engage one another while the second sled detent and the second mating detent engage one another.

Clause 15

15. The surgical staple cartridge of clause 12, wherein the cartridge body defines one of the first mating detent or the second mating detent and the cartridge pan defines the other of the first mating detent or the second mating detent.

Clause 16

16. A staple cartridge configured to be at least partially seated within a cartridge jaw of a surgical stapler, wherein the staple cartridge includes:

(a) a staple cartridge body; and (b) a sled slidably coupled with the staple cartridge body and drivable distally from a proximal undisplaced position to deploy staples from the staple cartridge body, wherein the sled includes a first detent and a second detent, wherein each of the first and second detents is configured to inhibit the sled from translating relative to the staple cartridge body, wherein the first detent and the second detent are axially aligned with one another parallel to a longitudinal axis of the staple cartidge.

Clause 17

17. The staple cartridge of clause 16, wherein each of the first detent and the second detent includes a profile extending along a length of each of the respective first and second detents.

Clause 18

18. The staple cartridge of clause 16, wherein each of the first and second detents is configured to engage respective protrusions of the staple cartridge body upon a distal translation of the sled relative to the staple cartridge body.

Clause 19

19. The staple cartridge of clause 16, wherein the first detent and the second detent are configured to engage the staple cartridge body in a proximal-most position of the sled relative to the staple cartridge body.

Clause 20

20. A method of inhibiting premature firing of a surgical staple cartridge having a cartridge body, a cartridge sled actuatable distally through the cartridge body to eject staples, and a cartridge pan, the method comprising:

(a) engaging the cartridge sled with a first mating detent defined by one of the cartridge body or the cartridge pan to releasably retain the cartridge sled in a first longitudinal position;

(b) permitting the sled to translate distally from the first longitudinal position such that the cartridge sled disengages the first mating detent; and (c) engaging the cartridge sled with a second mating detent defined by one of the cartridge body or the cartridge pan to releasably retain the cartridge sled in a second longitudinal position distal to the first longitudinal position.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A sled for a surgical stapler, the sled comprising:

(a) a base configured to translate distally relative to a jaw of the surgical stapler through a firing stroke to eject a plurality of staples into tissue;

(b) a plurality of rails extending upwardly from the base and configured to guide distal translation of the sled within the jaw through the firing stroke;

(c) a first sled detent positioned on a lateral half of the sled; and (d) a second sled detent positioned on the lateral half of the sled, wherein each of the first and second sled detents is configured to independently inhibit the sled from translating distally relative to the jaw prior to the firing stroke.

2. The sled of claim 1, wherein the first sled detent is configured to releasably retain the sled in a first pre-fired position and the second sled detent is configured to releasably retain the sled in a second pre-fired position distal to the first pre-fired position.

3. The sled of claim 1, wherein the first sled detent comprises one of a detent protrusion or a detent opening configured to releasably engage the other of a detent protrusion or a detent opening to inhibit distal translation of the sled, and wherein the second sled detent comprises a second detent protrusion or a second detent opening configured to releasably engage the other of a detent protrusion or a detent opening to inhibit distal translation of the sled independently from the first sled detent.

4. The sled of claim 1, wherein the plurality of rails defines at least one of the first sled detent or the second sled detent.

5. The sled of claim 1, wherein the base defines the first sled detent and a rail of the plurality of rails defines the second sled detent.

6. The sled of claim 1, wherein the plurality of rails defines the first sled detent and the second sled detent.

7. The sled of claim 1, wherein the first and second sled detents are configured to engage respective protrusions of a staple cartridge body upon a distal translation of the sled relative to the staple cartridge body.

8. The sled of claim 7, wherein the first sled detent is positioned distal to the second sled detent.

9. The sled of claim 1, wherein the first sled detent and the second sled detent are configured to engage a first protrusion and a second protrusion, respectively, of a staple cartridge body to thereby inhibit distal translation of the sled relative to the staple cartridge body.

10. The sled of claim 1, wherein each of the first detent and the second detent is positioned along a tallest portion of the sled.

11. A surgical staple cartridge, comprising:

(a) a cartridge body that houses a plurality of staples;

(b) a cartridge pan that encloses at least a portion of an underside of the cartridge body;

(c) the sled of claim 1, wherein the sled is slidably disposed between the cartridge body and the cartridge pan; and (d) a mating detent defined by one of the cartridge body or the cartridge pan and configured to releasably engage at least one of the first sled detent or the second sled detent to inhibit distal translation of the sled relative to the cartridge body prior to the firing stroke.

12. The surgical staple cartridge of claim 11, wherein the mating detent comprises a first mating detent and is configured to releasably engage the first sled detent to inhibit distal translation of the sled, further comprising a second mating detent longitudinally offset from the first mating detent and configured to releasably engage the second sled detent to inhibit distal translation of the sled independently from the first sled detent and the first mating detent.

13. The surgical staple cartridge of claim 12, wherein the first and second sled detents are spaced apart by a first longitudinal distance and the first and second mating detents are spaced apart by a second longitudinal distance that is unequal to the first longitudinal distance such that the first sled detent and the first mating detent are configured to engage one another while the second sled detent and the second mating detent are disengaged from one another and such that the second sled detent and the second mating detent are configured to engage one another while the first sled detent and the first mating detent are disengaged from one another.

14. The surgical staple cartridge of claim 12, wherein the first and second sled detents are spaced apart by a longitudinal distance and the first and second mating detents are also spaced apart by the longitudinal distance such that first sled detent and the first mating detent are configured to engage one another while the second sled detent and the second mating detent engage one another.

15. The surgical staple cartridge of claim 12, wherein the cartridge body defines one of the first mating detent or the second mating detent and the cartridge pan defines the other of the first mating detent or the second mating detent.

16. A staple cartridge configured to be at least partially seated within a cartridge jaw of a surgical stapler, wherein the staple cartridge includes:

(a) a staple cartridge body; and (b) a sled slidably coupled with the staple cartridge body and drivable distally from a proximal undisplaced position to deploy staples from the staple cartridge body, wherein the sled includes a first detent and a second detent, wherein each of the first and second detents is configured to inhibit the sled from translating relative to the staple cartridge body, wherein the first detent and the second detent are axially aligned with one another parallel to a longitudinal axis of the staple cartridge.

17. The staple cartridge of claim 16, wherein each of the first detent and the second detent includes a profile extending along a length of each of the respective first and second detents.

18. The staple cartridge of claim 16, wherein each of the first and second detents is configured to engage respective protrusions of the staple cartridge body upon a distal translation of the sled relative to the staple cartridge body.

19. The staple cartridge of claim 16, wherein the first detent and the second detent are configured to engage the staple cartridge body in a proximal-most position of the sled relative to the staple cartridge body.

20. A method of inhibiting premature firing of a surgical staple cartridge having a cartridge body, a cartridge sled actuatable distally through the cartridge body to eject staples, and a cartridge pan, the method comprising:

(a) engaging the cartridge sled with a first mating detent defined by one of the cartridge body or the cartridge pan to releasably retain the cartridge sled in a first longitudinal position;

(b) permitting the sled to translate distally from the first longitudinal position such that the cartridge sled disengages the first mating detent; and (c) engaging the cartridge sled with a second mating detent defined by one of the cartridge body or the cartridge pan to releasably retain the cartridge sled in a second longitudinal position distal to the first longitudinal position.

* * * * *